US012559781B2

(12) United States Patent
Arena et al.

(10) Patent No.: US 12,559,781 B2
(45) Date of Patent: Feb. 24, 2026

(54) METHODS OF PRODUCING POLYPEPTIDES USING A CELL LINE RESISTANT TO APOPTOSIS

(71) Applicant: Genentech, Inc., South San Francisco, CA (US)

(72) Inventors: Tia Alexandra Arena, San Francisco, CA (US); Athena W. Wong, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 1067 days.

(21) Appl. No.: 17/342,244

(22) Filed: Jun. 8, 2021

(65) Prior Publication Data

US 2021/0317501 A1 Oct. 14, 2021

Related U.S. Application Data

(63) Continuation of application No. PCT/US2019/067455, filed on Dec. 19, 2019.

(60) Provisional application No. 62/784,051, filed on Dec. 21, 2018.

(51) Int. Cl.
| | |
|---|---|
| *C12P 21/00* | (2006.01) |
| *C07K 14/47* | (2006.01) |
| *C12N 5/071* | (2010.01) |
| *C12N 15/86* | (2006.01) |
| *C12P 21/02* | (2006.01) |

(52) U.S. Cl.
CPC .......... *C12P 21/02* (2013.01); *C07K 14/4747* (2013.01); *C12N 5/0686* (2013.01); *C12N 15/86* (2013.01); *C12N 2510/02* (2013.01)

(58) Field of Classification Search
None
See application file for complete search history.

(56) References Cited

U.S. PATENT DOCUMENTS

| | | | | |
|---|---|---|---|---|
| 8,597,912 B2 * | 12/2013 | Collingwood | ....... | C12N 5/0018 435/69.7 |
| 2017/0114381 A1 | 4/2017 | Goudar et al. | | |

FOREIGN PATENT DOCUMENTS

| | | |
|---|---|---|
| CN | 106480090 A | 3/2017 |
| WO | 2009151591 A2 | 12/2009 |
| WO | 2009151591 A3 | 3/2010 |
| WO | 2013063379 A1 | 5/2013 |
| WO | 2018223108 A1 | 12/2018 |

OTHER PUBLICATIONS

Cost et al (Biotecnology and Bioengineering, 2010, 105:330-340).*
Jäger et al (BMC Biotechnology, 2013, 13:52, internet pp. 1-20).*
Zhang et al (Biotechnology and Bioengineering, 2017, 114:2539-2549).*
Vallée et al (Journal of Biotechnology, 2014, 169:63-70).*
Zhang et al.(2009); Use of Orbital Shaken Disposable Bioreactors for Mammalian Cell Cultures from the Milliliter-Scale to the 1,000-Liter Scale. pp. 33-53, In: Eibl, R., Eibl, D. (eds) Disposable Bioreactors. Advances in Biochemical Engineering / Biotechnology, vol. 115. Springer, Berlin, Heidelberg.*
Molinas et al (Cytotechnology, 2014, 66:493-514).*
Cervera et al (Appl. Microbiol. Biotechnol., 2015, 99:9935-9949).*
Yang et al (Molecular Cellular Biochemistry, 2015, 402:203-211).*
Abaandou, L. et al. (2021). "Affecting HEK293 Cell Growth and Production Performance by Modifying the Expression of Specific Genes," Cells 10:1667, 21 pages.
Arena, T. (Jan. 17, 2019). "Scaling Up a High-Titer HEK293 Transient Transfection Process," PepTalk: The Protein Science Week (Oral Presentation), p. 57. 61 total pages.
Arena, T.A. et al. (2019, e-pub. Apr. 24, 2019). "An Anti-Apoptotic HEK293 Cell Line Provides a Robust and High Titer Platform for Transient Protein Expression in Bioreactors," MABS 11(5):977-986.
Backliwal, G. et al. (2008, e-pub. Aug. 6, 2007). "High-Density Transfection With HEK-293 Cells Allows Doubling of Transient Titers and Removes Need for a Priori DNA Complex Formation With PEI," Biotechnol. Bioeng. 99(3):721-727.
Bertschinger, M. et al. (2008, e-pub. Jun. 10, 2008). "The Kinetics of Polyethylenimine-Mediated Transfection in Suspension Cultures of Chinese Hamster Ovary Cells," Mol. Biotechnol. 40(2):136-143.
Bláha, J. et al. (2015, e-pub. Jan. 24, 2015). "Expression and Purification of Soluble and Stable Ectodomain of Natural Killer Cell Receptor LLT1 Through High-Density Transfection of Suspension Adapted HEK293S GnTI-Cells," Protein Expr. Purif. 109:7-13.
Bos, A.B. et al. (2014, e-pub. Apr. 1, 2014). "Development of a Semi-Automated High Throughput Transient Transfection System," Journal of Biotechnology 180:10-16.
Bos, A.B. et al. (2015, e-pub. Jul. 7, 2015). "Optimization and Automation of an End-to-End High Throughput Microscale Transient Protein Production Process," Biotechnol.Bioeng. 112(9):1832-1842.
Callesen, M.M. et al. (2016). "Recombinase-Mediated Cassette Exchange (RMCE)-in Reporter Cell Lines as an Alternative to the Flp-in System," PLoS One 11:e0161471, 14 pages.
Chandra, D. e al. (2005, e-pub. Mar. 9, 2005). "Bax-Dependent Regulation of Bak By Voltage-Dependent Anion Channel 2," J. Biol. Chem. 280(19):19051-19061.
Chiou, H.C. et al., (2014). "Scalable Transient Protein Expression," Methods Mol. Biol. 1104:35-55.
Choosakoonkriang, S. et al. (2003). "Biophysical Characterization of PEI/DNA Complexes," Journal of Pharmaceutical Sciences 92(8):1710-1722.
Cost, G.J. et al. (2010, e-pub. Sep. 23, 2009). "BAK and BAX Deletion Using Zinc-Finger Nucleases Yields Apoptosis-Resistant CHO Cells," Biotechnology and Bioengineering 105(2):330-340.
Croset, A. al. (2012, e-pub. Jul. 16, 2012). "Differences in the Glycosylation of Recombinant Proteins Expressed in HEK and CHO Cells," J. Biotechnol. 161(3):336-348.

(Continued)

*Primary Examiner* — Laura B Goddard

(74) *Attorney, Agent, or Firm* — MORRISON & FOERSTER LLP

(57) ABSTRACT

Provided herein are cell lines (e.g., HEK293 cell lines) that comprise a loss-of-function mutation in each of the human Bax and Bak genes, as well as cell cultures comprising the cell lines. The cell lines and/or cell cultures may find use, e.g., in methods for producing a recombinant polypeptide (such as an antibody or antigen-binding fragment thereof) or a viral vector.

8 Claims, 27 Drawing Sheets

(56) References Cited

OTHER PUBLICATIONS

Delafosse, L. et al. (2016, e-pub. Apr. 13, 2016). "Comparative Study of Polyethylenimines for Transient Gene Expression in Mammalian HEK293 and CHO Cells," J. Biotechnol. 227:103-111.

Ding, K. et al. (2017, e-pub. Nov. 16, 2016). "Production Process Reproducibility and Product Quality Consistency of Transient Gene Expression in HEK293 Cells With Anti-PD1 Antibody as the Model Protein," Appl. Microbiol. Biotechnol. 101(5):1889-1898.

Girard, P. et al. (2001). "Small-Scale Bioreactor System for Process Development and Optimization," Biochem. Eng. J. 7(2):117-119.

Graham, F.L. et al. (1977). "Characteristics of a Human Cell Line Transformed by DNA From Human Adenovirus Type 5," Journal General Virology 36(1):59-74.

Grav, L.M. et al. (2015, e-pub. Apr. 30, 2015). "One-Step Generation of Triple Knockout CHO Cell Lines Using CRISPR/Cas9 and Fluorescent Enrichment," Biotechnology Journal 10(9):1446-1456.

Ho, S.C.L. et al. (2013). "Generation of Monoclonal Antibody-Producing Mammalian Cell Lines," Pharmaceutical Bioprocessing 1(1):71-87.

Hisu, W.T. et al. (2012, e-pub. Mar. 27, 2012). "Advanced Microscale Bioreactor System: A Representative Scale-Down Model for Bench-Top Bioreactors," Cytotechnology 64:667-678.

International Preliminary Report on Patentability, issued Jun. 16, 2021, for PCT Application No. PCT/US2019/067455, filed Dec. 19, 2019, 9 pages.

International Search Report and Written Opinion, mailed Mar. 16, 2020, for PCT Application No. PCT/US2019/067455, filed Dec. 19, 2019, 13 pages.

Jain, N.K. et al. (2017, e-pub. Mar. 23, 2017). "A High Density CHO-S Transient Transfection System: Comparison of ExpiCHO and Expi293," Protein Expr. Purif. 134:38-46.

Lewis, G. et al. (2010), "Novel Automated Micro-Scale Bioreactor Technology: A Qualitative and Quantitative Mimic for Early Process Development," Bioprocessing J. 9:22-25.

Li, F. et al. (2010). "Cell Culture Processes for Monoclonal Antibody Production," Mabs 2(5):466-477.

Li, J. et al. (2012, e-pub. Nov. 28, 2011). "Feeding Lactate for CHO Cell Culture Processes: Impact on Culture Metabolism and Performance," Biotechnol. Bioeng. 109(5):1173-1186.

Lim, S.F. et al. (2006, e-pub. Jun. 7, 2006). "RNAi Suppression of BAX and BAK Enhances Viability in Fed-Batch Cultures of CHO Cells," Metabolic Engineering 8(6):509-522.

Lin, Y.-C. et al. (2014). "Genome Dynamics of the Human Embryonic Kidney 293 Lineage in Response to Cell Biology Manipulations," Nat. Commun. 5:4767, 12 pages.

Liste-Calleja, L. et al. (2015, e-pub. Aug. 14, 2015). "Lactate and Glucose Concomitant Consumption as a Self-Regulated pH Detoxification Mechanism in HEK293 Cell Cultures," Appl. Microbiol. Biotechnol. 99(23):9951-9960.

Louis, N. et al. (1997). "Cloning and Sequencing of the Cellular-Viral Junctions from the Human Adenovirus Type 5 Transformed 293 Cell Line," Virology 233:423-429.

Macaraeg, N.F. et al. (2013, e-pub. Jun. 22, 2013). "Use of an Anti-Apoptotic CHO Cell Line for Transient Gene Expression," Biotechnology Progress 29(4):1050-1058.

Meissner, P. et al. (2001). "Transient Gene Expression: Recombinant Protein Production With Suspension-Adapted HEK293-EBNA Cells," Biotechnology and Bioengineering 75(2):197-203.

Misagahi, S. et al. (2013 e-pub. Apr. 18, 2013). "Resilient Immortals, Characterizing and Utilizing BAX/BAK Deficient Chinese Hamster Ovary (CHO) Cells for High Titer Antibody Production," Biotechnology Progress 29(3):727-737.

Mollet, M. et al. (2007, e-pub. May 11, 2007). "Acute Hydrodynamic Forces and Apoptosis: A Complex Question," Biotechnol. Bioeng. 98(4):772-788.

NCBI Accession No. NP_001179.1 (Jun. 26, 2021). BCL-2 Homologous Antagonist/Killer [Homo sapiens], 3 pages.

NCBI Accession No. NP_001278357.1 (Nov. 28, 2021). Apoptosis Regulator BAX Isoform 1 [Homo sapiens], 3 pages.

NCBI Accession No. NP_001278358.1 (Nov. 28, 2021). Apoptosis Regulator BAX Isoform Gamma [Homo sapiens], 3 pages.

NCBI Accession No. NP_001278359.1 (Dec. 2, 2021). Apoptosis Regulator BAX Isoform Lambda [Homo sapiens], 3 pages.

NCBI Accession No. NP_001278360.1 (Nov. 28, 2021). Apoptosis Regulator BAX Isoform Zeta [Homo sapiens], 3 pages.

NCBI Accession No. NP_004315.1 (Nov. 28, 2021). Apoptosis Regulator BAX Isoform Beta [Homo sapiens], 3 pages.

NCBI Accession No. NP_620116.1 (Nov. 28, 2021). Apoptosis Regulator BAX Isoform Alpha [Homo sapiens], 3 pages.

NCBI Accession No. NP_620118.1 (Nov. 28, 2021). Apoptosis Regulator BAX Isoform Delta [Homo sapiens], 3 pages.

NCBI Accession No. NP_620119.2 (Nov. 28, 2021). Apoptosis Regulator BAX Isoform Sigma [Homo sapiens], 3 pages.

NCBI Accession No. XP_011513081.1 (Nov. 22, 2021). BCL-2 Homologous Antagonist/Killer Isoform X1 [Homo sapiens], 2 pages.

NCBI Accession No. XP_011513082.1 (Nov. 22, 2021). BCL-2 Homologous Antagonist/Killer Isoform X2 [Homo sapiens], 2 pages.

NCBI Accession No. XP_016882566.1 (Nov. 22, 2021). Apoptosis Regulator BAX Isoform X1 [Homo sapiens], 2 pages.

Nettelship, J.E. et al. (2010, e-pub. Feb. 11, 2010). "Recent Advances in the Production of Proteins in Insect and Mammalian Cells for Structural Biology," J. Struct. Biol. 172(1):55-65.

Qiao, C. et al. (2002). "A Novel Gene Expression Control System and Its Use in Stable, High-Titer 293 Cell-Based Adeno-Associated Virus Packaging Cell Lines," J. Virol. 76(24):13015-13027.

Rajendra, Y. et al. (2011, e-pub. Mar. 8, 2011). "A Simple High-Yielding Process for Transient Gene Expression in CHO Cells," J. Biotechnol. 153(1-2):22-26.

Rajendra, Y. et al. (2015, e-pub. Mar. 16, 2015). "A High Cell Density Transient Transfection System for Therapeutic Protein Expression Based on a CHO GS-Knockout Cell Line: Process Development and Product Quality Assessment," Biotechnol. Bioeng. 112(5):977-986.

Raymond, C. et al. (2011, e-pub. Apr. 24, 2011). "A Simplified Polyethylenimine-Mediated Transfection Process for Large-Scale and High-Throughput Applications," Methods 55(1):44-51.

Rockberg, J. et al. (2018). "Production of Biopharmaceuticals in an Intensified Perfusion Process of HEK 293 Cells," Cell Culture Engineering XVI, 1 page.

Sun, X. et al. (2008, e-pub. Jul. 13, 2007). "High-Density Transient Gene Expression in Suspension-Adapted 293 EBNA1 Cells," Biotechnol. Bioeng. 99(1):108-116.

Taylor, R.C. et al. (2008). "Apoptosis: Controlled Demolition at the Cellular Level," Nat. Rev. Mol. Cell Biol. 9(3):231-241.

Vink, T. et al. (2014, e-pub. Jul. 17, 2013). "A Simple, Robust and Highly Efficient Transient Expression System for Producing Antibodies," Methods 65:5-10.

Yuan, Z. et al. (2011). "A Versatile Adeno-Associated Virus Vector Producer Cell Line Method for Scalable Vector Production of Different Serotypes," Hum. Gene Ther. 22:613-624.

Yuk, I.H. et al. (2011) "Overcoming Challenges in WAVE Bioreactors Without Feedback Controls for pH and Dissolved Oxygen," Biotechnol. Prog. 27(5):1397-1406.

Zhang, W. et al. (2017, e-pub. Aug. 17, 2017). "Generation of Apoptosis-Resistant HEK293 Cells With CRISPR/Cas Mediated Quadruple Gene Knockout for Improved Protein and Virus Production," Biotechnology and Bioengineering 114(11):2539-2549.

Zhao, Y. et al. (2011). "Automation of Large Scale Transient Protein Expression in Mammalian Cells," J. Struct. Biol. 175(2-2):209-215, 13 pages.

Zin, N.K.M. et al. (2016). "Controlling Shear Stress in Suspension Culture Using Couette Flow for Efficient Proliferation of HEK 293 Cells," Fluid Mechanics: Open Access 3(1):1000124, 5 pages.

* cited by examiner

FIG. 4E

METHODS OF PRODUCING POLYPEPTIDES USING A CELL LINE RESISTANT TO APOPTOSIS

CROSS-REFERENCE TO RELATED APPLICATIONS

This application is a continuation of International Application No. PCT/US2019/067455, filed Dec. 19, 2019, which claims the priority benefit of U.S. Provisional Application No. 62/784,051, filed Dec. 21, 2018, each of which is hereby incorporated by reference in its entirety.

FIELD

This disclosure relates to methods of producing a recombinant polypeptide or viral vector, as well as cell lines and cell cultures that may find use, e.g., in said methods.

BACKGROUND

Monoclonal antibodies (mAbs) and other recombinant proteins have been established as successful therapeutics for many disease indications including immunology, oncology, neuroscience, and others (see, e.g., Reichert (2017) *mAbs.* 9:167-181; Singh et al. (2017) *Curr. Clin. Pharmacol.* 13:85-99). With over 300 mAbs in development in the biotechnology industry, the mAb market is projected to expand to 70 mAb products by the year 2020 (Ecker et al. (2015) *mAbs.* 7:9-14). As the industry expands and targets become more complex, larger antibody discovery campaigns are needed to screen multiple mAb variants and identify clinical candidates with the desired characteristics.

Transient transfection of mammalian cells using the cationic polymer polyethylenimine (PEI) has become a prevalent method to rapidly produce recombinant proteins for large molecule development, including antibody discovery screening studies (Baldi et al. (2007) *Biotechnol. Lett.* 29:677-684; Hacker et al. (2013) *Protein Expr. Purif.* 92:67-76; Stuible et al. (2018) *J. Biotechnol.* 281:39-47; Longo et al. (2013) *Meth. Enzymol.* 529:227-240; Rajendra et al. (2015) *Biotechnol. Prog.* 31:541-549). Human embryonic kidney 293 (HEK293) and Chinese hamster ovary (CHO) host cells are often used for transient transfections because they are highly transfectable and their transfection processes are scalable.

While HEK293 product quality may differ compared to that from CHO cells (Ding et al. (2017) *Appl. Microbiol. Biotechnol.* 101:1889-1898), HEK293 transfections can produce higher titers in half the time compared to CHO (Delafosse et al. (2016) *J. Biotechnol.* 227:103-111; Chiou et al., (2014) Scalable transient protein expression. In: Portner editor. Animal cell biotechnology: Methods and protocols. Totowa, NJ: Humana Press. p. 35-55) and are very amenable to high throughput, automated small scale transfections (Vink et al. (2014) *Methods* 65:5-10; Bos et al. (2014) *J. Biotechnol.* 180:10-16; Zhao et al. (2011) *J. Struct. Biol.* 175:209-215; Girard et al. (2001) *Biochem. Eng. J.* 7:117-119; Raymond et al. (2011) *Methods* 55:44-51; Nettelship et al. (2010) 1 Struct. Biol. 172:55-65). While there are numerous reports describing CHO large scale bioreactor cultivation and transfections, fewer findings exist for HEK293 cells and there are currently no reports of long term cultivation of HEK293 seed train in bioreactors to support routine, high throughput transfections to generate large quantities of proteins.

All references cited herein, including patent applications, patent publications, and UniProtKB/Swiss-Prot Accession numbers are herein incorporated by reference in their entirety, as if each individual reference were specifically and individually indicated to be incorporated by reference.

SUMMARY

There remains a need for optimal methods for culturing human cell lines, such as HEK293-derived cell lines, in order to produce recombinant polynucleotides and/or polypeptides. In particular, HEK293 cells have been found to be sensitive to shear stress with low viabilities when cultured in bioreactors; HEK293 culture sensitivity to shear stress has also been reported in spinner flasks (Mohd Zin et al. (2016) *Fluid Mechanics: Open Access* 3:1-5) and hollow fiber filters (Rockberg et al. (2018) Production of biopharmaceuticals in an intensified perfusion process of HEK 293 cells. Paper presented at: Cell Culture Engineering XVI. Tampa, Florida, USA). As such, a need exists for a HEK293 cell line with resistance to apoptosis in order to provide higher productivity and more robust performance in bioreactors.

To meet these and other demands, provided herein are HEK293 cell lines comprising a loss-of-function mutation in each of the human Bax and Bak genes. Advantageously, these cell lines and cultures thereof may find use in the production of recombinant polynucleotide and/or polypeptide products, including without limitation antibodies (or antigen-binding antibody fragments), antigens, enzymes, vaccines, and viral vectors.

In one aspect, provided herein are methods of producing a recombinant polypeptide comprising culturing a HEK293 cell line that comprises (a) a loss-of-function mutation in each of the human Bax and Bak genes and (b) a polynucleotide encoding the recombinant polypeptide under conditions suitable for production of the polypeptide. In some embodiments, the polynucleotide that encodes the recombinant polypeptide is an extrachromosomal polynucleotide. In some embodiments, the polynucleotide that encodes the recombinant polypeptide is integrated into a chromosome of the HEK293 cell line. In some embodiments, the recombinant polypeptide is an antibody or antigen-binding fragment thereof, an antigen, an enzyme, or a vaccine. In some embodiments, the recombinant polypeptide is an antibody or antigen-binding fragment thereof (e.g., a diagnostic or therapeutic antibody or antigen-binding fragment thereof). In some embodiments, the cell line produces the recombinant polypeptide at a titer of about 650 mg/L in 7 days. In some embodiments, the methods further comprise isolating the recombinant polypeptide from the cell line.

In another aspect, provided herein are methods of producing a viral vector, comprising culturing a HEK293 cell line that comprises (a) a loss-of-function mutation in each of the human Bax and Bak genes, (b) a viral genome, and (c) one or more polynucleotides encoding a viral capsid under conditions suitable for production of the viral vector. In some embodiments, the methods further comprise isolating the viral vector from the cell line.

In some embodiments of any of the above embodiments, the cell line is cultured in a cell culture medium. In some embodiments, the cell line is cultured at a pH of between about 6.7 and about 7.3, between about 6.9 and about 7.1, between about 6.95 and about 7.05, or about 7.0. In some embodiments, the cell line is cultured with a dissolved oxygen (DO) setpoint of about 30%. In some embodiments, the cell line is cultured at an agitation rate that imparts a power input per volume (P/V) of about 13 $W/m^3$. In some embodiments, the cell line is cultured in a volume of at least about 10 L. In some embodiments, the cell line is cultured in a volume of at least about 25 L. In some embodiments, the cell line is cultured in a 35 L bioreactor. In some embodiments, the methods comprise culturing the cell line in a 35 L bioreactor for 60 days. In some embodiments, the cell line maintains at least 85% cell viability after culturing the cell line for 60 days in a 35 L bioreactor. In some embodiments, the cell line is cultured in the 35 L bioreactor at a working volume of between about 20 L and about 35 L. In some embodiments, the cell line is cultured under fed-batch culture conditions. In some embodiments, the cell line is cultured under perfusion culture conditions.

In another aspect, provided herein are cell cultures comprising a cell culture medium and a plurality of HEK293 cells, wherein each cell of the plurality comprises a loss-of-function mutation in each of the human Bax and Bak genes. In some embodiments, the cells are at a cell density sufficient for a 35 L bioreactor culture. In some embodiments, the cells are maintained at a cell density sufficient for a 35 L bioreactor culture for 60 days. In some embodiments, the cell line maintains at least 85% cell viability after culturing the cell line for 60 days in a 35 L bioreactor culture. In some embodiments, the plurality of cells maintains greater than 75% cell viability after exposure to a shear stress of $2.67 \times 10^7$ W/m$^3$ energy dissipation rate (EDR). In some embodiments, the plurality of cells maintains greater than 75% cell viability after exposure to 1 µM staurosporine for 70 hours. In some embodiments, each cell of the plurality comprises a deletion in each of the Bax and Bak genes. In some embodiments, the cell line further comprises a polynucleotide that encodes a recombinant polypeptide. In some embodiments, the polynucleotide that encodes the recombinant polypeptide is an extrachromosomal polynucleotide. In some embodiments, the polynucleotide that encodes the recombinant polypeptide is integrated into a chromosome of the human cell line. In some embodiments, the recombinant polypeptide is an antibody or antigen-binding fragment thereof, an antigen, an enzyme, or a vaccine. In some embodiments, the recombinant polypeptide is an antibody or antigen-binding fragment thereof (e.g., a diagnostic or therapeutic antibody or antigen-binding fragment thereof). In some embodiments, the cell culture produces the recombinant polypeptide at a titer of about 650 mg/L in 7 days. In some embodiments, the cell line further comprises a recombinant polynucleotide.

In another aspect, provided herein is a HEK293 cell line (e.g., an isolated HEK293 cell line) that comprises a loss-of-function mutation in each of the human Bax and Bak genes. In some embodiments, the cell line comprises a deletion in each of the Bax and Bak genes. In some embodiments, the cell line further comprises a viral genome and one or more polynucleotides encoding a viral capsid. In some embodiments, the cell line further comprises a polynucleotide encoding a recombinant polypeptide. In some embodiments, the polynucleotide that encodes the recombinant polypeptide is an extrachromosomal polynucleotide. In some embodiments, the polynucleotide that encodes the recombinant polypeptide is integrated into a chromosome of the human cell line. In some embodiments, the recombinant polypeptide is an antibody or antigen-binding fragment thereof, an antigen, an enzyme, or a vaccine. In some embodiments, the recombinant polypeptide is an antibody or antigen-binding fragment thereof (e.g., a diagnostic or therapeutic antibody or antigen-binding fragment thereof). In some embodiments, the cell line produces a higher titer of the recombinant polypeptide than a corresponding isolated human cell line that comprises the polynucleotide and functional copies of each of the human Bax and Bak genes. In some embodiments, the cell line is more resistant to shear stress than a corresponding isolated human cell line that comprises functional copies of each of the human Bax and Bak genes. In some embodiments, the cell line is more resistant to apoptosis than a corresponding isolated human cell line that comprises functional copies of each of the human Bax and Bak genes. In some embodiments, the cell line is more resistant to staurosporine than a corresponding isolated human cell line that comprises functional copies of each of the human Bax and Bak genes.

In another aspect, provided herein are cell cultures comprising the cell line according to any one of the above embodiments and a cell culture medium.

It is to be understood that one, some, or all of the properties of the various embodiments described herein may be combined to form other embodiments of the present disclosure. These and other aspects of the disclosure will become apparent to one of skill in the art. These and other embodiments of the disclosure are further described by the detailed description that follows.

BRIEF DESCRIPTION OF THE DRAWINGS

FIG. 1A shows cell viability after exposure of the cell lines to 1 µM staurosporine to induce apoptosis. FIGS. 1B-1D show the effects of using a flow constriction device (FCD) to assess sensitivity of the DKO and parental cell lines to shear stress on total lysis after FCD (FIG. 1B), viable cell density (VCD) before and after FCD (FIG. 1C), and viability before and after FCD (FIG. 1D).

FIGS. 2B & 2C show the effects of transfecting HEK293 and HEK293 DKO cells at the 30 mL tubespin scale with an N:P ratio of 7.5 and a DNA concentration of 1 µg/mL on viable cell density (VCD) (FIG. 2B) and viability over the 7 day production cultures and day 7 titers (FIG. 2C).

(FIG. 3A) viable cell density (VCD) and viability, (FIG. 3B) glucose and lactate, (FIG. 3C) offline pH, and (FIG. 3D) pO$_2$. (FIG. 3E) Day 7 transfection titers from 30 mL tubespins.

(FIG. 4A) viable cell density (VCD) and viability, (FIG. 4B) glucose and lactate, and (FIG. 4C) offline pH. (FIG. 4D) Day 7 transfection titers from 30 mL tubespins.

FIGS. 4E-4N show product quality attributes on day 7 after HEK293 DKO cells were transfected in 30 mL tubespins using cells sourced from the 1 L shake flask and the 35 L bioreactor seed train over 60 days. Glycosylation species: (FIG. 4E) Glycosylation species analyzed, (FIG. 4F) G0F, (FIG. 4G) G1F, (FIG. 4H) G2F, (FIG. 4I) G0, and (FIG. 4L)

M5. Charge variants: (FIG. 4J) acidic, (FIG. 4M) main, and (FIG. 4K) basic. Size variants: (FIG. 4N) high molecular weight species (HMWS).

(FIG. 5A) Viable cell density (VCD) and viability, (FIG. 5B) glucose and lactate, (FIG. 5C) osmolality and pH, (FIG. 5D) pO$_2$, and (FIG. 5E) titers over the 7 day production cultures.

(FIG. 6A) Viable cell density (VCD) and viability, (FIG. 6B) glucose and lactate, (FIG. 6C) osmolality and pH, and (FIG. 6D) pO$_2$ over the 7 day production cultures. (FIG. 6E) Day 7 titers.

DETAILED DESCRIPTION

Figure 1A:
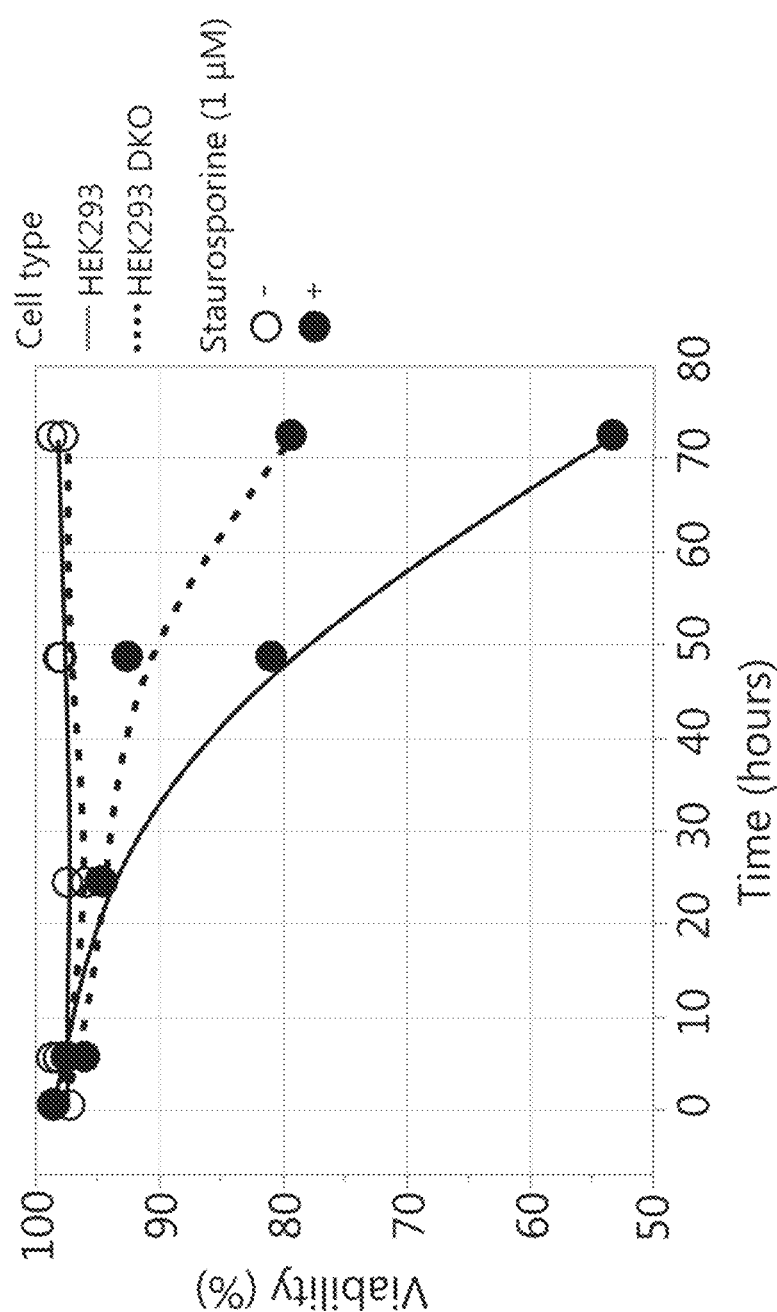
FIGS. 1A-1D compare the HEK293 DKO cell line (with Bax and Bak genes knocked out as described in Example 1) to the parental HEK293 cell line.

The present disclosure provides cell lines (e.g., HEK293 cell lines) with improved resistance to apoptosis and shear stress. These cell lines were demonstrated to exhibit robust performance in a bioreactor (e.g., a seed train bioreactor) and allow for long-term cultivation of a human cell line at a 35 L pilot scale in a stirred tank bioreactor or improved production in a 10 L wavebag bioreactor. As such, the cell lines of the present disclosure may find use, e.g., in cell cultures and methods of cell culturing (such as methods of recombinant polynucleotide, recombinant polypeptide, and viral vector production).

In one aspect, provided herein are methods of producing a recombinant polypeptide comprising culturing a HEK293 cell line that comprises (a) a loss-of-function mutation in each of the human Bax and Bak genes and (b) a polynucleotide encoding the recombinant polypeptide under conditions suitable for production of the polypeptide.

In another aspect, provided herein are methods of producing a viral vector, comprising culturing a HEK293 cell line that comprises (a) a loss-of-function mutation in each of the human Bax and Bak genes, (b) a viral genome, and (c) one or more polynucleotides encoding a viral capsid under conditions suitable for production of the viral vector.

In another aspect, provided herein are cell cultures comprising a cell culture medium and a plurality of HEK293 cells, wherein each cell of the plurality comprises a loss-of-function mutation in each of the human Bax and Bak genes.

In another aspect, provided herein is a HEK293 cell line (e.g., an isolated HEK293 cell line) that comprises a loss-of-function mutation in each of the human Bax and Bak genes.

I. Definitions

Before describing the disclosure in detail, it is to be understood that this disclosure is not limited to particular compositions or biological systems, which can, of course, vary. It is also to be understood that the terminology used herein is for the purpose of describing particular embodiments only, and is not intended to be limiting.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se. At a maximum, the term "about" as used herein in reference to a value, encompasses from 90% to 110% of that value (e.g., relative translation strength of a first and second TIR of about 1.0 to about 3.0 refers to a relative translation strength in the range of between 0.9 and 3.3).

It is understood that aspects and embodiments of the disclosure described herein include "comprising," "consisting," and "consisting essentially of" aspects and embodiments.

The term "polynucleotide," when used in singular or plural, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "polypeptide" or "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component or toxin. Also included within the definition are, for example, polypeptides containing one or more analogs of an amino acid (including, for example, unnatural amino acids, etc.), as well as other modifications known in the art. The terms "polypeptide" and "protein" as used herein specifically encompass antibodies.

A "loss-of-function mutation" in a gene refers to a genetic manipulation or mutation (e.g., a substitution, deletion, insertion, duplication, frameshift, or translocation) in a gene that reduces or eliminates one or more functions of the corresponding gene product. In some embodiments, the loss-of-function mutation is a null mutation that eliminates one or more functions of the corresponding gene product, e.g., a deletion that removes some or all of the coding sequence. In some embodiments, the loss-of-function mutation refers to a genetic manipulation that leads to a reduction in the expression of a gene, e.g., knockdown by RNAi (e.g., siRNA or shRNA), CRISPRi, miRNA, morpholino, etc.

The term "recombinant," when used to modify a polynucleotide, polypeptide, or viral vector, refers to a polynucleotide/polypeptide/viral vector that has been introduced into, or has been produced by, a host cell that does not naturally contain or produce the polynucleotide/polypeptide/viral vector. The polynucleotide, polypeptide, or viral vector itself may be non-naturally occurring (e.g., a humanized antibody), or it may exist in nature, but not in the context of the host cell (e.g., a human antibody produced by a human cell type that does not typically generate antibodies in nature).

The term "host cell" (or "recombinant host cell"), as used herein, is intended to refer to a cell that has been genetically altered, or is capable of being genetically altered by introduction of an exogenous or non-native polynucleotide, such as a recombinant plasmid or vector. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, a "HEK293 cell line" refers to any cell whose lineage can ultimately be traced back to the original HEK293 cell line, e.g., the cell line represented by ATCC catalog number CRL-1573™ and/or generated upon transforming human embryonic kidney cells with fragments of adenovirus type 5 DNA as described (Graham et al. (1977) *J. Gen. Virol.* 36:59-74). The term includes HEK293 cell lines that have been genetically modified, e.g., by introducing mutations in the Bax and Bak genes and optionally transfected with a recombinant polynucleotide and/or infected with a viral vector (e.g., a recombinant viral vector). The HEK293 cell line is known to be pseudotriploid with a 4 kb adenoviral genome fragment integrated into chromosome 19 (Louis et al. (1997) *Virology* 233:423-429). Features of the HEK293 genome and transcriptome have been described (Lin et al. (2014) *Nat. Commun.* 5:4767 doi: 10.1038/ncomms5767).

"Culture medium" (the term "cell culture medium" can be used interchangeably herein) as used herein refers to any composition or broth that supports the growth of a cell line of the present disclosure. Suitable culture media may be liquid or solid and contain any nutrients, salts, buffers, elements, and other compounds that support the growth and viability of cells. Common nutrients of a culture medium may include sources of nitrogen, carbon, amino acids, carbohydrates, trace elements, vitamins, and minerals. These nutrients may be added as individual components (as in a defined culture medium) or as constituents of a complex extract (for example, yeast extract, or plant/animal hydrolysates or peptides). A culture medium can include animal-derived components such as serum, or it can be animal origin-free. A culture medium can be chemically defined. A culture medium may be nutrient-rich to support rapid growth or minimal to support slower growth. A culture medium may also contain any agent used to inhibit the growth of or kill contaminating organisms (e.g., an antibiotic or antimycotic). A culture medium may also contain any compound used to control the activity of an inducible promoter or enzyme.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The term "constant domain" refers to the portion of an immunoglobulin molecule having a more conserved amino acid sequence relative to the other portion of the immunoglobulin, the variable domain, which contains the antigen binding site. The constant domain contains the $C_H1$, $C_H2$ and $C_H3$ domains (collectively, CH) of the heavy chain and the CHL (or CL) domain of the light chain.

The "variable region" or "variable domain" of an antibody refers to the amino-terminal domains of the heavy or light chain of the antibody. The variable domain of the heavy chain may be referred to as "$V_H$." The variable domain of the light chain may be referred to as "$V_L$." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any mammalian species can be assigned to one of two clearly distinct types, called kappa ("κ") and lambda ("λ"), based on the amino acid sequences of their constant domains.

The term IgG "isotype" or "subclass" as used herein is meant any of the subclasses of immunoglobulins defined by the chemical and antigenic characteristics of their constant regions.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, γ, ε, γ, and μ, respectively. The subunit structures and three-dimensional configurations of different classes of immunoglobulins are well known and described generally in, for example, Abbas et al. *Cellular and Mol. Immunology*, 4th ed. (W.B. Saunders, Co., 2000). An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fc region.

A "naked antibody" for the purposes herein is an antibody that is not conjugated to a cytotoxic moiety or radiolabel.

"Antibody fragments" comprise a portion of an intact antibody, preferably comprising the antigen binding region thereof. In some embodiments, the antibody fragment described herein is an antigen-binding fragment. Examples of antibody fragments include Fab, Fab', $F(ab')_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this disclosure. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, e.g., Vaswani and Hamilton, *Ann. Allergy, Asthma & Immunol.* 1:105-115 (1998); *Harris, Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227: 381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

TABLE 1a

| Antibody Hypervariable Regions | | | | |
| --- | --- | --- | --- | --- |
| Loop | Kabat | AbM | Chothia | Contact |
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., *Sequences of Immunological Interest*. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody.

The expression "linear antibodies" refers to the antibodies described in Zapata et al. (1995 *Protein Eng,* 8(10):1057-1062). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

II. Cell Lines

Provided herein are HEK293 cell lines (e.g., isolated HEK293 cell lines) that comprise a loss-of-function mutation in each of the human Bax and Bak genes.

The human Bax gene (also known as Bcl214) encodes a pro-apoptotic Bcl-2 family member. During apoptosis, Bax and Bak permeate the mitochondrial membrane, leading to loss of membrane potential and the release of cytochrome c, which ultimately leads to the activation of caspase proteins that trigger programmed cell death (Taylor et al. (2008) *Nat. Rev. Mol. Cell Biol.* 9:231-241). Either Bax or Bak is required to permeabilize the mitochondrial outer membrane during the mitochondrial or intrinsic pathway of apoptosis. In some embodiments, the human Bax gene refers to the gene described by NCBI Gene ID No. 581. In some embodiments, the human Bax gene encodes one or more of the following human Bax isoforms: X1 (see, e.g., NCBI Accession No. XP_016882566.1), zeta (see, e.g., NCBI Accession No. NP_001278360.1), lambda (see, e.g., NCBI Accession No. NP_001278359.1), gamma (see, e.g., NCBI Accession No. NP_001278358.1), 1 (see, e.g., NCBI Accession No. NP_001278357.1), sigma (see, e.g., NCBI Accession No. NP_620119.2), delta (see, e.g., NCBI Accession No. NP_620118.2), alpha (see, e.g., NCBI Accession No. NP_620116.2), and beta (see, e.g., NCBI Accession No. NP_004315.1).

The human Bak gene (also known as BCL2 antagonist/killer 1, Bak1, Cdn1, Bcl217, and Bak-like) encodes a pro-apoptotic Bcl-2 family member. During apoptosis, Bax and Bak permeate the mitochondrial membrane, leading to loss of membrane potential and the release of cytochrome c, which ultimately leads to the activation of caspase proteins that trigger programmed cell death (Taylor et al. (2008) *Nat. Rev. Mol. Cell Biol.* 9:231-241). In some embodiments, the human Bak gene refers to the gene described by NCBI Gene ID No. 578. In some embodiments, the human Bak gene encodes one or more of the following human Bak isoforms: X1 (see, e.g., NCBI Accession No. XP 011513082.1), X2 (see, e.g., NCBI Accession No. XP_011513081.1), and the standard isoform (see, e.g., NCBI Accession No. NP_001179.1).

In some embodiments, the loss-of-function mutation comprises one or more substitution, insertion, deletion, and/or frameshift mutations. In some embodiments, the loss-of-function mutation comprises a deletion. Various loss-of-function mutations in the human Bax and Bak genes are known. For example, Bax and Bak mutations have been described in various cancers; see, e.g., OMIM entries 600040 and 600516 and COSMIC (Catalogue of Somatic Mutations in Cancer) entries for Bax and Bak (cancer-.sanger.ac.uk/cosmic/gene/analysis? ln=BAX and cancer-.sanger.ac.uk/cosmic/gene/analysis? ln=BAK1, respectively). In some embodiments, a loss-of-function mutation in Bax or Bak reduces or eliminates one or more functions of Bax or Bak (e.g., pro-apoptotic functions), including but not limited to promotion of apoptosis, loss of mitochondrial membrane potential, outer mitochondrial membrane pore formation, and release of cytochrome c. In some embodiments, a loss-of-function mutation in Bax or Bak reduces or eliminates expression of Bax or Bak protein. In some embodiments, a loss-of-function mutation in Bax or Bak refers to a genetic manipulation that reduces or eliminates expression of Bax or Bak protein, e.g., by RNAi, CRISPRi, miRNA, morpholino, etc. In some embodiments, a loss-of-function mutation in Bax inhibits sensitivity to apoptosis and/or loss of mitochondrial membrane potential, outer mitochondrial membrane pore formation, or release of cytochrome c in a cell with a loss-of-function mutation in Bak, and/or a loss-of-function mutation in Bak inhibits sensitivity to apoptosis and/or loss of mitochondrial membrane potential, outer mitochondrial membrane pore formation, or release of cytochrome c in a cell with a loss-of-function mutation in Bax. For example, it has been demonstrated that reducing Bak function when Bax function is impaired has a much more dramatic effect on sensitivity to apoptosis than reducing Bak function in the context of normal Bax function (see, e.g., Chandra, D. et al. (2005) *J. Biol. Chem.* 280:19051-19061).

Techniques for engineering a HEK293 cell line with a loss-of-function mutation in each of the human Bax and Bak genes are known. In some embodiments, as exemplified herein, zinc finger nuclease technology (Cost et al. (2010) *Biotechnol. Bioeng.* 105:330-340) can be used to introduce loss-of-function mutations (e.g., deletions) in Bax and Bak. Other techniques for introducing mutations in a human cell include, without limitation, CRISPR/Cas9, TALEN, site-directed mutagenesis by PCR, chemical mutagenesis, insertional mutagenesis, and so forth.

In some embodiments, a HEK293 cell line that comprises a loss-of-function mutation in each of the human Bax and Bak genes displays one or more of the following, as compared with a HEK293 cell line that comprises functional copies of each of the human Bax and Bak genes, or a HEK293 cell line that comprises a functional copy of only one of the human Bax and Bak genes: increased resistance to apoptosis, increased resistance to shear stress, increased resistance to staurosporine, and increased production of a recombinant polypeptide (e.g., in cell culture).

Recombinant Polynucleotides, Polypeptides, Antigens, Enzymes, and Vaccines

In some embodiments, a cell line of the present disclosure (e.g., a HEK293 cell line comprising a loss-of-function mutation in each of the human Bax and Bak genes) comprises a recombinant polynucleotide. For example, in some embodiments, the recombinant polynucleotide encodes a recombinant polypeptide (e.g., one or more chains of an antibody or antibody fragment).

In some embodiments, a recombinant polynucleotide (e.g., a recombinant polynucleotide that encodes a recombinant polypeptide) is an extrachromosomal polynucleotide. In some embodiments, the recombinant polynucleotide is introduced into the cell line without integration of the polynucleotide into the host cell genome. In some embodiments, the recombinant polynucleotide is introduced into the cell line by transient transfection. Transient transfection is known to introduce recombinant polynucleotide(s) into a cell line without integration of the polynucleotide(s) into the host cell genome; as such, the polynucleotide(s) are not replicated along with the host cell genome and are lost after a finite period of time (due to, e.g., cell division, degradation, etc.). Methods for transiently transfecting HEK293 cell lines are known in the art (see, e.g., de Los Milagros Bassani Molinas et al. (2014) *Cytotechnology* 66:493-514) and kits for transient transfection of HEK293 cells are commercially available (see, e.g., the Expi293™ Expression System for transient HEK293 cell transfection sold by Thermo Fisher Scientific).

In other embodiments, a recombinant polynucleotide (e.g., a recombinant polynucleotide that encodes a recombinant polypeptide) is integrated into the host cell genome, e.g., onto a chromosome of the human cell line. In some embodiments, the recombinant polynucleotide is introduced into the cell line by stable transfection. Stable transfection is known to introduce recombinant polynucleotide(s) into a cell line through stable inheritance of non-genomic DNA or the incorporation of the recombinant polynucleotide(s) into the host cell genome (e.g., by integration onto a host cell chromosome). In some embodiments, a recombinant polynucleotide is integrated into the host cell genome by random integration. For example, the recombinant polynucleotide can encode a selectable marker (e.g., encoding a protein that confers resistance to an antibiotic such as puromycin, hygromycin, G418, etc.), and cells transfected with the recombinant polynucleotide can be subjected to one or more rounds of selection via the selectable marker (e.g., by using a cell culture medium comprising an antibiotic such as puromycin, hygromycin, G418, etc. to kill cells that do not express the selectable marker). Techniques and kits for random integration into HEK293 cells are known in the art; see, e.g., www.thermofisher.com/us/en/home/references/gibco-cell-culture-basics/transfection-basics/transfection-methods/stable-transfection.html. In some embodiments, a recombinant polynucleotide is integrated into the host cell genome by site-specific or targeted integration. For example, a technique such as recombinase-mediated cassette exchange (RMCE), Cre-Lox recombination, or FLP-FRT recombination can be used to integrate a recombinant polynucleotide into a targeted site in the host cell genome. Techniques and kits for using site-specific or targeted integration in HEK293 cells are known in the art (see, e.g., Callesen et al. (2016) *PLoS One* 11:e0161471) and the Flp-In™ 293 cell line (Thermo Fisher Scientific).

In some embodiments, a recombinant polynucleotide of the present disclosure encodes a recombinant polypeptide. Exemplary recombinant polypeptides are listed infra. In some embodiments, a recombinant polypeptide produced by a HEK293 cell line of the present disclosure comprises one or more post-translational modifications (e.g., glycosylation) characteristic of production in a human cell, e.g., as compared to the modifications of a comparable polypeptide produced in a prokaryotic, fungal, insect, or non-human mammalian cell. For example, differences in glycosylation between similar proteins expressed in HEK293 cells vs. CHO cells have been documented (see, e.g., Croset et al. (2012) *J. Biotechnol.* 161:336-348). In some embodiments, a recombinant polypeptide produced by a HEK293 cell line of the present disclosure comprises a glycosylation modification comprising one or more of the exemplary and non-limiting glycans shown in FIG. 4E.

In some embodiments, a recombinant polynucleotide of the present disclosure encodes an antigen. In some embodiments, the antigen is a polypeptide antigen. In some embodiments, the antigen is a peptide antigen. In some embodiments, the antigen is a therapeutic or diagnostic antigen.

In some embodiments, a recombinant polynucleotide of the present disclosure encodes an enzyme. In some embodiments, the enzyme is a therapeutic or diagnostic enzyme.

In some embodiments, a recombinant polynucleotide of the present disclosure encodes a vaccine. In some embodiments, the vaccine is a peptide vaccine. In some embodiments, the vaccine is a live-attenuated, inactivated, toxoid, or subunit/recombinant vaccine. In some embodiments, the vaccine is against one or more of: measles, mumps, rubella, rotavirus, smallpox, chickenpox, yellow fever, hepatitis A, hepatitis B, influenza, polio, rabies, Hib disease, human papillomavirus, whooping cough, pneumococcal disease, meningococcal disease, shingles, tetanus, and diphtheria.

In some embodiments, a recombinant polynucleotide of the present disclosure comprises a viral genome and/or encodes a viral capsid. As described in greater detail in section IV infra, the cell lines of the present disclosure may find use, inter alia, in methods of producing viral vectors. In some embodiments, a cell line of the present disclosure comprises a viral genome (e.g., of a viral vector of interest) and one or more polynucleotides encoding a viral capsid. For example, HEK293 cell lines have been modified to include in their genome AAV genes (e.g., Rep and Cap genes) to generate packaging cell lines that can then be infected with adenovirus for the production of adeno-associated virus (AAV) vectors (see, e.g., Qiao et al. (2002) *J. Virol.* 76:13015-13027). HEK293 cell lines have also been modified to include in their genome AAV genes (e.g., Rep and Cap genes) as well as adenovirus genes (e.g., E1A/E1B) to generate producer cell lines for the production of adeno-associated virus (AAV) vectors (see, e.g., Yuan et al. (2011) *Hum. Gene Ther.* 22:613-624).

In some embodiments, the recombinant polynucleotide comprises an expression vector. An expression vector can include one or more of the following elements: a signal sequence, an origin of replication, one or more marker genes, an enhancer element, a promoter, and a transcription termination sequence.

A recombinant polypeptide of the present disclosure may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (e.g., cleaved by a signal peptidase) by the host cell. In mammalian cell expression, mammalian signal sequences as well as viral secretory leaders, for example, the herpes simplex gD signal, are available.

In some embodiments, an expression vector comprises an origin of replication. Generally, in vectors this sequence is one that enables the vector to replicate independently of the host chromosomal DNA, and includes origins of replication or autonomously replicating sequences. Generally, the origin of replication component is not needed for mammalian expression vectors (the SV40 origin may typically be used only because it contains the early promoter. In other embodiments, the vector does not include an origin of replication (e.g., if the recombinant polynucleotide is integrated onto a host cell chromosome).

In some embodiments, as alluded to above with regard to stable transfections, an expression vector comprises a selection gene or selectable marker. Typical selection genes encode proteins that (a) confer resistance to antibiotics or other toxinse, (b) complement auxotrophic deficiencies, or (c) supply critical nutrients not available from complex media. One example of a selection scheme utilizes a drug to arrest growth of a host cell. Those cells that are successfully transformed with a heterologous gene produce a protein conferring drug resistance and thus survive the selection regimen. Another example of suitable selectable markers for mammalian cells are those that enable the identification of cells competent to take up antibody-encoding nucleic acid, such as DHFR, glutamine synthetase (GS), thymidine kinase, metallothionein-I and -II, preferably primate metal-lothionein genes, adenosine deaminase, ornithine decar-boxylase, etc. For example, cells transformed with the DHFR gene are identified by culturing the transformants in a culture medium containing methotrexate (Mtx), a com-petitive antagonist of DHFR. Under these conditions, the DHFR gene is amplified along with any other co-trans-formed nucleic acid. Alternatively, cells transformed with the GS gene are identified by culturing the transformants in a culture medium containing L-methionine sulfoximine (Msx), an inhibitor of GS. Under these conditions, the GS gene is amplified along with any other co-transformed nucleic acid. The GS selection/amplification system may be used in combination with the DHFR selection/amplification system described above. Alternatively, host cells (particu-larly wild-type hosts that contain endogenous DHFR) trans-formed or co-transformed with DNA sequences of interest, wild-type DHFR gene, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

In some embodiments, an expression vector comprises a promoter. Expression and cloning vectors generally contain a promoter that is recognized by the host organism and is operably linked to the recombinant polynucleotide. Anti-body transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepati-tis-B virus, Simian Virus 40 (SV40), or from heterologous mammalian promoters, e.g., the actin promoter or an immu-noglobulin promoter, from heat-shock promoters, provided such promoters are compatible with the host cell systems. The early and late promoters of the SV40 virus are conve-niently obtained as an SV40 restriction fragment that also contains the SV40 viral origin of replication. The immediate early promoter of the human cytomegalovirus is conve-niently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

In some embodiments, an expression vector comprises an enhancer element. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the antibody-encoding sequence, but is preferably located at a site 5' from the promoter.

In some embodiments, an expression vector comprises a transcription terminator, e.g., sequence(s) necessary for the termination of transcription and for stabilizing the mRNA. Such sequences are commonly available from the 5' and, occasionally 3', untranslated regions of eukaryotic or viral DNAs or cDNAs. These regions contain nucleotide seg-ments transcribed as polyadenylated fragments in the untranslated portion of the mRNA encoding antibody. One useful transcription termination component is the bovine growth hormone polyadenylation region. See WO94/11026 and the expression vector disclosed therein.

Antibodies and Antibody Fragments

In some embodiments, a recombinant polynucleotide of the present disclosure encodes an antibody or antigen-binding fragment thereof. For example, in some embodi-ments, the recombinant polynucleotide encodes the heavy and light chains for an antibody or antibody fragment, or a single chain antibody or antibody fragment. Exemplary methods for using a cell line or cell culture of the present disclosure to produce an antibody or antibody fragment are described in greater detail in section IV infra.

In some embodiments, the antibody (or antibody frag-ment) is a diagnostic antibody. For example, the antibody can be used to detect one or more diagnostic antigens in a sample, e.g., by ELISA, Western blotting, immunohisto-chemistry (IHC), flow cytometry, or other immunoassays. As non-limiting examples, diagnostic antibodies have been used to detect HER2 (see, e.g., the HercepTest for identi-fying tumors that overexpress HER2 from DAKO Corp.), the estrogen and progesterone receptors (see, e.g., the ER/PR pharmDx kit for identifying tumors that overexpress ER or PR from DAKO Corp.), and PD-L1 (see, e.g., the Ventana SP263 and SP142 assays for identifying tumors that express PD-L1) for diagnostic assays used, e.g., in the treatment of various cancers.

In some embodiments, the antibody (or antibody frag-ment) is a therapeutic antibody. Exemplary therapeutic anti-bodies include, without limitation, nivolumab (OPDIVO®, Bristol-Myers Squibb), pembrolizumab (KEYTRUDA®, Merck),avelumab (BAVENCIO®, Merck), durvalumab (IMFINZI®, Astra-Zeneca/Medimmune), alemtuzumab (Campath), bevacizumab (AVASTIN®, Genentech); cetux-imab (ERBITUX®, Imclone); panitumumab (VECTIBIX®, Amgen), rituximab (RITUXAN®, Genentech/Biogen Idec), pertuzumab (PERJETA®, 2C4, Genentech), trastuzumab (HERCEPTIN®, Genentech), atezolizumab (TECEN-TRIQ®, Genentech), obinutuzumab (GAZYVA®, Genen-tech), ocrelizumab (OCREVUS®, Genentech), tositumo-mab (Bexxar, Corixia), gemtuzumab ozogamicin (MYLOTARG®, Wyeth), apolizumab, aselizumab, atli-zumab, bapineuzumab, bivatuzumab mertansine, can-tuzumab mertansine, cedelizumab, certolizumab pegol, cidfusituzumab, cidtuzumab, daclizumab, eculizumab, efali-zumab, epratuzumab, erlizumab, felvizumab, fontolizumab, gemtuzumab ozogamicin, inotuzumab ozogamicin, ipilim-umab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, resli-zumab, resyvizumab, rovelizumab, ruplizumab, sibro-tuzumab, siplizumab, sontuzumab, tacatuzumab tetraxetan, tadocizumab, talizumab, tefibazumab, tocilizumab, toralizumab, tucotuzumab celmoleukin, tucusituzumab, umavi-zumab, urtoxazumab, ustekinumab, visilizumab, and the anti-interleukin-12 (ABT-874/J695, Wyeth Research and Abbott Laboratories) which is a recombinant exclusively human-sequence, full-length $IgG_1$ $\lambda$ antibody genetically modified to recognize interleukin-12 p40 protein. A non-limiting list of monoclonal antibodies approved by the EMA or FDA for therapeutic use can be found at www.actip.org/products/monoclonal-antibodies-approved-by-the-ema-and-fda-for-therapeutic-use/.

Features of antibodies and antibody fragments are described in a non-limiting manner infra.

Certain Antibody-Based Methods

Monoclonal antibodies can be made using the hybridoma method first described by Kohler et al., *Nature*, 256:495 (1975), and further described, e.g., in Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981), and Ni, *Xiandai Mianyixue*, 26(4):265-268 (2006) regarding human-human hybridomas. Additional methods include those described, for example, in U.S. Pat. No. 7,189,826 regarding production of monoclonal human natural IgM antibodies from hybridoma cell lines. Human hybridoma technology (Trioma technology) is described in Vollmers and Brandlein, *Histology and Histopathology*, 20(3):927-937 (2005) and Vollmers and Brandlein, *Methods and Findings in Experimental and Clinical Pharmacology*, 27(3): 185-91 (2005). Once desired monoclonal antibodies have been isolated from hybridomas, polynucleotides encoding them may be subcloned into an expression vector, and antibodies may be produced by expression in a HEK293 cell line by any of the methods described herein.

Library-Derived Antibodies

Antibodies of the disclosure may be isolated by screening combinatorial libraries for antibodies with the desired activity or activities. For example, a variety of methods are known in the art for generating phage display libraries and screening such libraries for antibodies possessing the desired binding characteristics such as the methods described in Example 3. Additional methods are reviewed, e.g., in Hoogenboom et al. in *Methods in Molecular Biology* 178:1-37 (O'Brien et al., ed., Human Press, Totowa, NJ, 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, NJ, 2003); Sidhu et al., *J Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

Chimeric, Humanized and Human Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA*, 89:4285 (1992); and Presta et al. *J. Immunol.*, 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008). Human antibodies can be made, for example and without limitation, by expression in a HEK293 cell line from an expression vector by any of the methods described herein.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Antibody Fragments

Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. (2003) *Nat. Med.* 9:129-134.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')₂ fragments (Carter et al., *Bio/Technology* 10:163-167 (1992)). According to another approach, F(ab')₂ fragments can be isolated directly from recombinant host cell culture. Fab and F(ab')₂ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See *Antibody Engineering*, ed. Borrebaeck, supra. The antibody fragment may also be a "linear antibody", e.g., as described in U.S. Pat. No. 5,641,870, for example. Such linear antibodies may be monospecific or bispecific.

Multispecific Antibodies

Multispecific antibodies have binding specificities for at least two different epitopes, where the epitopes are usually from different antigens. While such molecules normally will only bind two different epitopes (i.e. bispecific antibodies, BsAbs), antibodies with additional specificities such as trispecific antibodies are encompassed by this expression when used herein. Bispecific antibodies can be prepared as full length antibodies or antibody fragments (e.g. F(ab')₂ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature,* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.,* 10:3655-3659 (1991).

One approach known in the art for making bispecific antibodies is the "knobs-into-holes" or "protuberance-into-cavity" approach (see, e.g., U.S. Pat. No. 5,731,168). In this approach, two immunoglobulin polypeptides (e.g., heavy chain polypeptides) each comprise an interface. An interface of one immunoglobulin polypeptide interacts with a corresponding interface on the other immunoglobulin polypeptide, thereby allowing the two immunoglobulin polypeptides to associate. These interfaces may be engineered such that a "knob" or "protuberance" (these terms may be used interchangeably herein) located in the interface of one immunoglobulin polypeptide corresponds with a "hole" or "cavity" (these terms may be used interchangeably herein) located in the interface of the other immunoglobulin polypeptide. In some embodiments, the hole is of identical or similar size to the knob and suitably positioned such that when the two interfaces interact, the knob of one interface is positionable in the corresponding hole of the other interface. Without wishing to be bound to theory, this is thought to stabilize the heteromultimer and favor formation of the heteromultimer over other species, for example homomultimers. In some embodiments, this approach may be used to promote the heteromultimerization of two different immunoglobulin polypeptides, creating a bispecific antibody comprising two immunoglobulin polypeptides with binding specificities for different epitopes.

In some embodiments, a knob may be constructed by replacing a small amino acid side chain with a larger side chain. In some embodiments, a hole may be constructed by replacing a large amino acid side chain with a smaller side chain. Knobs or holes may exist in the original interface, or they may be introduced synthetically. For example, knobs or holes may be introduced synthetically by altering the nucleic acid sequence encoding the interface to replace at least one "original" amino acid residue with at least one "import" amino acid residue. Methods for altering nucleic acid sequences may include standard molecular biology techniques well known in the art. The side chain volumes of various amino acid residues are shown in the following table. In some embodiments, original residues have a small side chain volume (e.g., alanine, asparagine, aspartic acid, glycine, serine, threonine, or valine), and import residues for forming a knob are naturally occurring amino acids and may include arginine, phenylalanine, tyrosine, and tryptophan. In some embodiments, original residues have a large side chain volume (e.g., arginine, phenylalanine, tyrosine, and tryptophan), and import residues for forming a hole are naturally occurring amino acids and may include alanine, serine, threonine, and valine.

TABLE 1b

Properties of amino acid residues

| Amino Acid | One-letter abbreviation | Mass[a] (daltons) | Volume[b] (Å$^3$) | Accessible surface area[c] (Å$^2$) |
|---|---|---|---|---|
| Alanine (Ala) | A | 71.08 | 88.6 | 115 |
| Arginine (Arg) | R | 156.20 | 173.4 | 225 |
| Asparagine (Asn) | N | 114.11 | 117.7 | 160 |
| Aspartic Acid (Asp) | D | 115.09 | 111.1 | 150 |
| Cysteine (Cys) | C | 103.14 | 108.5 | 135 |
| Glutamine (Gln) | Q | 128.14 | 143.9 | 180 |
| Glutamic Acid (Glu) | E | 129.12 | 138.4 | 190 |
| Glycine (Gly) | G | 57.06 | 60.1 | 75 |
| Histidine (His) | H | 137.15 | 153.2 | 195 |
| Isoleucine (Ile) | I | 113.17 | 166.7 | 175 |
| Leucine (Leu) | L | 113.17 | 166.7 | 170 |
| Lysine (Lys) | K | 128.18 | 168.6 | 200 |
| Methionine (Met) | M | 131.21 | 162.9 | 185 |
| Phenylalanine (Phe) | F | 147.18 | 189.9 | 210 |
| Proline (Pro) | P | 97.12 | 122.7 | 145 |
| Serine (Ser) | S | 87.08 | 89.0 | 115 |
| Threonine (Thr) | T | 101.11 | 116.1 | 140 |
| Tryptophan (Trp) | W | 186.21 | 227.8 | 255 |
| Tyrosine (Tyr) | Y | 163.18 | 193.6 | 230 |
| Valine (Val) | V | 99.14 | 140.0 | 155 |

[a]Molecular weight of amino acid minus that of water. Values from Handbook of Chemistry and Physics, 43$^{rd}$ ed. Cleveland, Chemical Rubber Publishing Co., 1961.
[b]Values from Zamyatnin, Prog. Biophys. Mol. Biol. 24: 107-123, 1972.
[c]Values from Chothia, J. Mol. Biol. 105: 1-14, 1975. The accessible surface area is defined in FIGS. 6-20 of this reference.

In some embodiments, original residues for forming a knob or hole are identified based on the three-dimensional structure of the heteromultimer. Techniques known in the art for obtaining a three-dimensional structure may include X-ray crystallography and NMR. In some embodiments, the interface is the CH3 domain of an immunoglobulin constant domain. In these embodiments, the CH3/CH3 interface of human IgG$_1$ involves sixteen residues on each domain located on four anti-parallel β-strands. Without wishing to be bound to theory, mutated residues are preferably located on the two central anti-parallel β-strands to minimize the risk that knobs can be accommodated by the surrounding solvent, rather than the compensatory holes in the partner CH3 domain. In some embodiments, the mutations forming corresponding knobs and holes in two immunoglobulin polypeptides correspond to one or more pairs provided in the following table.

TABLE 2

Exemplary sets of corresponding knob-and hole-forming mutations

| CH3 of first immunoglobulin | CH3 of second immunoglobulin |
|---|---|
| T366Y | Y407T |
| T366W | Y407A |
| T366W | T366S:L368A:Y407V |
| F405A | T394W |
| Y407T | T366Y |
| T366Y:F405A | T394W:Y407T |
| T366W:F405W | T394S:Y407A |
| F405W:Y407A | T366W:T394S |
| F405W | T394S |

Mutations are denoted by the original residue, followed by the position using the Kabat numbering system, and then the import residue (all residues are given in single-letter amino acid code). Multiple mutations are separated by a colon.

In some embodiments, an immunoglobulin polypeptide comprises a CH3 domain comprising one or more amino acid substitutions listed in Table 2 above. In some embodiments, a bispecific antibody comprises a first immunoglobulin polypeptide comprising a CH3 domain comprising one or more amino acid substitutions listed in the left column of Table 2, and a second immunoglobulin polypeptide comprising a CH3 domain comprising one or more corresponding amino acid substitutions listed in the right column of Table 2. As a non-limiting example of a knob-and-hole-forming pair, in some embodiments, a bispecific antibody comprises a first immunoglobulin polypeptide comprising a CH3 domain comprising a T366 W mutation, and a second immunoglobulin polypeptide comprising a CH3 domain comprising T366S, L368A, and Y407V mutations.

Each half-antibody can have either a knob (protuberance) or a hole (cavity) engineered into the heavy chain as described in U.S. Pat. No. 7,642,228. Briefly, a CH3 knob mutant can be generated first. A library of CH3 hole mutants can be then created by randomizing residues 366, 368 and 407 that are in proximity to the knob on the partner CH3 domain. In certain embodiments, the knob mutation comprises T366 W, and the hole mutations comprise T366S, L368A and Y407V in an IgG1 or IgG4 backbone. Equivalent mutations in other immunoglobulin isotypes can be made by one skilled in the art. Further, the skilled artisan will readily appreciate that it is preferred that the two half-antibodies used for the bispecific antibody be of the same isotype.

Exemplary and non-limiting techniques for producing multispecific (e.g., bispecific) antibodies are provided in section IV.

Antibodies with more than two valencies are contemplated. For example, trispecific antibodies can be prepared. Tuft et al. *J. Immunol.* 147: 60 (1991).

In some embodiments, the two chain protein is a part of a multispecific antibody or a bispecific antibody. A multispecific antibody or a bispecific antibody may contain two or more monovalent antibodies of the present disclosure.

In some embodiments, the first antigen binding domain of the bispecific antibody comprises one or more heavy chain constant domains, wherein the one or more heavy chain constant domains are selected from a first CH1 (CH1$_1$) domain, a first CH2 (CH2$_1$) domain, a first CH3 (CH3$_1$) domain; and the second antigen binding domain of the bispecific antibody comprises one or more heavy chain constant domains, wherein the one or more heavy chain constant domains are selected from a second CH1 (CH1$_2$) domain, second CH2 (CH2$_2$) domain, and a second CH3 (CH3$_2$) domain. In some embodiments, at least one of the one or more heavy chain constant domains of the first antigen binding domain is paired with another heavy chain constant domain of the second antigen binding domain. In some embodiments, the CH3$_1$ and CH3$_2$ domains each comprise a protuberance or cavity, and wherein the protuberance or cavity in the CH3$_1$ domain is positionable in the cavity or protuberance, respectively, in the CH3$_2$ domain. In some embodiments, the CH3$_1$ and CH3$_2$ domains meet at an interface between said protuberance and cavity. Examplary sets of amino acid substitutions in CH3$_1$ and CH3$_2$ domains are shown in Table 2 herein. In some embodiments, the CH2$_1$ and CH2$_2$ domains each comprise a protuberance or cavity, and wherein the protuberance or cavity in the CH2$_1$ domain is positionable in the cavity or protuberance, respectively, in the CH2$_2$ domain. In some embodiments, the CH2$_1$ and CH2$_2$ domains meet at an interface between said protuberance and cavity. In some embodiments, the CH3$_1$ and/or CH3$_2$ domain of an IgG contain one or more amino acid substitutions at residues selected from the group consisting of 347, 349, 350, 351, 366, 368, 370, 392, 394, 395, 398, 399, 405, 407, and 409 according to the amino acid numbering as shown in FIG. 5 of the U.S. Pat. No. 8,216, 805. In some embodiments, the protuberance comprises one or more introduced residues selected from the group consisting of arginine (R) residue, phenylalanine (F) residue, tyrosine (Y) residue, and tryptophan (W) residue. In some embodiments, the cavity comprises one or more introduced residues selected from the group consisting of alanine (A) residue, serine (S) residue, threonine (T) residue, and valine (V) residue. In some embodiments, the CH3 and/or CH2 domains are from an IgG (e.g., IgG1 subtype, IgG2 subtype, IgG2A subtype, IgG2B subtype, IgG3, subtype, or IgG4 subtype). In some embodiments, one CH3 domain of the bispecific antibody comprises amino acid substitution T366Y, and the other CH3 domain comprises amino acid substitution Y407T. In some embodiments, one CH3 domain comprises amino acid substitution T366 W, and the other CH3 domain comprises amino acid substitution Y407A. In some embodiments, one CH3 domain comprises amino acid substitution F405A, and the other CH3 domain comprises amino acid substitution T394 W. In some embodiments, one CH3 domain comprises amino acid substitutions T366Y and F405A, and the other CH3 domain comprises amino acid substitutions T394 W and Y407T. In some embodiments, one CH3 domain comprises amino acid substitutions T366 W and F405 W, and the other CH3 domain comprises amino acid substitutions T394S and Y407A. In some embodiments, one CH3 domain comprises amino acid substitutions F405 W and Y407A, and the other CH3 domain comprises amino acid substitutions T366 W and T394S. In some embodiments, one CH3 domain comprises amino acid substitution F405 W, and the other CH3 domain comprises amino acid substitution T394S. The mutations are denoted by the original residue, followed by the position using the Kabat numbering system, and then the import residues. See also numbering in FIG. 5 of U.S. Pat. No. 8,216,805.

Single-Domain Antibodies

In some embodiments, an antibody of the disclosure is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). In one embodiment, a single-domain antibody consists of all or a portion of the heavy chain variable domain of an antibody.

Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the disclosure contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom et al., *Proc. Nat'l Acad. Sci. USA* 83:7059-7063 (1986)) and Hellstrom et al., *Proc. Nat'l Acad. Sci. USA* 82:1499-1502 (1985); U.S. Pat. No. 5,821,337 (see Bruggemann, et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg et al., *Blood* 101:1045-1052 (2003); and Cragg and Glennie, *Blood* 103:2738-2743 (2004)). FcRn binding and in vivo clearance/half life determinations can also be performed using methods known in the art (see, e.g., Petkova, et al., *Int'l. Immunol.* 18(12): 1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues). In an exemplary embodiment, the antibody comprising the following amino acid substitutions in its Fc region: S298A, E333A, and K334A.

In some embodiments, alterations are made in the Fc region that result in altered (i.e., either improved or diminished) C1q binding and/or Complement Dependent Cyto-toxicity (CDC), e.g., as described in U.S. Pat. No. 6,194,551, WO 99/51642, and Idusogie et al. *J. Immunol.* 164: 4178-4184 (2000).

Antibodies with increased half lives and improved bind-ing to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hin-ton et al.)). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, *Nature* 322:738-40 (1988); U.S. Pat. Nos. 5,648,260; 5,624,821; and WO 94/29351 concerning other examples of Fc region variants.

Antibody Derivatives

The antibodies of the disclosure can be further modified to contain additional nonproteinaceous moieties that are known in the art and readily available. In certain embodi-ments, the moieties suitable for derivatization of the anti-body are water soluble polymers. Non-limiting examples of water soluble polymers include, but are not limited to, polyethylene glycol (PEG), copolymers of ethylene glycol/propylene glycol, carboxymethylcellulose, dextran, polyvi-nyl alcohol, polyvinyl pyrrolidone, poly-1,3-dioxolane, poly-1,3,6-trioxane, ethylene/maleic anhydride copolymer, polyaminoacids (either homopolymers or random copoly-mers), and dextran or poly(n-vinyl pyrrolidone)polyethylene glycol, propropylene glycol homopolymers, prolypropylene oxide/ethylene oxide co-polymers, polyoxyethylated poly-ols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the anti-body may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

III. Cell Cultures

Provided herein are cell cultures comprising a HEK293 cell line (e.g., isolated HEK293 cell lines) that comprises a loss-of-function mutation in each of the human Bax and Bak genes. Any of the HEK293 cell lines of the present disclo-sure, including the exemplary cell lines described in section II supra, may find use in the cell cultures of the present disclosure.

In some embodiments, a cell culture of the present dis-closure comprises a plurality of HEK293 cells of the present disclosure and a cell culture medium. Cell culture media suitable for culturing HEK293 cells are known in the art and commercially available; see, e.g., FreeStyle™ 293 Expres-sion Medium (Gibco), Expi293™ Expression Medium (Gibco), and ATCC-formulated Eagle's Minimum Essential Medium (ATCC Cat. No. 30-2003), optionally supple-mented with serum. Cell culture media may be supple-mented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GEN-TAMYCIN™ drug), trace elements (defined as inorganic compounds usually present at final concentrations in the micromolar range), and glucose or an equivalent energy source. Any other necessary supplements may also be included at appropriate concentrations.

In some embodiments, the cells of the cell culture are at a cell density sufficient for a 35 L bioreactor culture. For example, in some embodiments, the cells of the cell culture are maintained at a cell density sufficient for a 35 L bioreactor culture for 7, 14, 21, 30, 45, or 60 days. In some embodiments, the cells of the cell culture are at a cell density between about $0.4 \times 10^6$ cells/mL and about $6 \times 10^6$ cells/mL (e.g., in a fed-batch culture). In some embodiments, the cells of the cell culture are at a cell density between about $0.4 \times 10^6$ cells/mL and about $1.0 \times 10^8$ cells/mL (e.g., in a perfusion culture).

In some embodiments, a cell culture of the present dis-closure maintains greater than 50%, greater than 60%, or greater than 75% cell viability after exposure to a shear stress of $2.67 \times 10^7$ W/m³ energy dissipation rate (EDR). In certain embodiments, a cell culture of the present disclosure maintains greater than 75% cell viability after exposure to a shear stress of $2.67 \times 10^7$ W/m³ energy dissipation rate (EDR). In some embodiments, cells of a cell culture of the present disclosure show less than 50%, less than 45%, less than 40%, less than 35%, or less than 30% total lysis after exposure to a shear stress of $2.67 \times 10^7$ W/m³ energy dissi-pation rate (EDR). Exemplary assays for exposing cells to shear stress include, without limitation, passing cells through a flow constriction device (FCD; Ma et al. (2002) *Biotechnol. Bioeng.* 75:197-203; and Mollet et al. (2007) *Biotechnol. Bioeng.* 98:772-788).

In some embodiments, cells of a cell culture of the present disclosure maintain greater than 50%, greater than 60%, greater than 75%, or greater than 80% cell viability after exposure to 1 µM staurosporine for 70 hours. In some embodiments, cells of a cell culture of the present disclosure maintain greater than 70%, greater than 75%, greater than 80%, or greater than 85% cell viability after exposure to 1 µM staurosporine for 60 hours. In some embodiments, cells of a cell culture of the present disclosure maintain greater than 80%, greater than 85%, or greater than 90% cell viability after exposure to 1 µM staurosporine for 50 hours. In certain embodiments, cells of a cell culture of the present disclosure maintain greater than 75% cell viability after exposure to 1 µM staurosporine for 70 hours.

In some embodiments, a cell culture of the present dis-closure (e.g., comprising a HEK293 cell line of the present disclosure that produces a recombinant polypeptide as described herein) produces a recombinant polypeptide (e.g., an antibody, such as a human IgG1 antibody) at a titer of at least about 500 mg/L, at least about 550 mg/L, at least about 600 mg/L, or a about 600 mg/L in 7 days. In certain embodiments, a cell culture of the present disclosure (e.g., comprising a HEK293 cell line of the present disclosure that produces a recombinant polypeptide as described herein) produces a recombinant polypeptide at a titer of about 650 mg/L in 7 days. In some embodiments, the HEK293 cell line is transiently transfected with a recombinant polynucleotide encoding the recombinant polypeptide. In some embodi-ments, the cell culture is a 30 mL cell culture (e.g., seeded at about $2 \times 10^6$ cells/mL).

IV. Methods of Production

Provided herein are methods of producing a recombinant polypeptide, comprising culturing a HEK293 cell line of the present disclosure that comprises a polynucleotide encoding the recombinant polypeptide under conditions suitable for production of the polypeptide. Also provided herein are methods of producing a viral vector, comprising culturing a HEK293 cell line of the present disclosure that comprises a viral genome and one or more polynucleotides encoding a viral capsid under conditions suitable for production of the viral vector.

Any of the cell lines of the present disclosure (e.g., as described in section II) or cell cultures of the present disclosure (e.g., as described in section III) may find use in the methods of the present disclosure. For example, in some embodiments, the cell line is a HEK293 cell line comprising a loss-of-function mutation in each of the human Bax and Bak genes.

In some embodiments, a cell line of the present disclosure is cultured in a cell culture medium. Exemplary and non-limiting cell culture media and descriptions of cell culture media are provided in section III supra.

In some embodiments, a cell line of the present disclosure is cultured at a pH of between about 6.7 and about 7.3, between about 6.8 and about 7.2, between about 6.9 and about 7.1, between about 6.95 and about 7.05, or about 7. In certain embodiments, a cell line of the present disclosure is cultured at a pH setpoint of 7.0 with a deadband of ±0.03. In some embodiments, culture pH is controlled using $CO_2$ as acid and 1 M sodium carbonate as base.

In some embodiments, a cell line of the present disclosure is cultured with a dissolved oxygen (DO) setpoint of about 30%. In some embodiments, culture DO is controlled by sparging with air and pure oxygen gas via an open pipe sparger.

In some embodiments, a cell line of the present disclosure is cultured at an agitation rate that imparts a power input per volume (P/V) of about 13 $W/m^3$. Power input per volume can be calculated using the formula:

$$\frac{P}{V} = \frac{P_{no}N^3D^5\rho}{V}$$

Where
$P_{no}$=Power number (specific to impeller geometry)
N=Agitation rate (rotations per second)
D=Impeller diameter (m)
$\rho$=Liquid density (kg/m^3)
V=Working volume (m^3)

In some embodiments, a cell line of the present disclosure is cultured in a volume of at least about 10 L, at least about 15 L, at least about 20 L, at least about 25 L, at least about 30 L, at least about 35 L, at least about 50 L, at least about 60 L, at least about 75 L, or about 100 L. In some embodiments, a cell line of the present disclosure is cultured in a volume of between about 10 L and about 35 L, between about 15 L and about 35 L, between about 20 L and about 35 L, between about 25 L and about 35 L, between about 35 L and about 100 L, or between about 10 L and about 100 L. In some embodiments, a cell line of the present disclosure is cultured in a bioreactor having a volume of at least about 10 L, at least about 15 L, at least about 20 L, at least about 25 L, at least about 30 L, or at least about 35 L. In some embodiments, a cell line of the present disclosure is cultured at a working volume of at least about 20 L, at least about 25 L, at least about 30 L, or at least about 35 L. In some embodiments, a cell line of the present disclosure is cultured at a working volume of between about 10 L and about 35 L, between about 15 L and about 35 L, between about 20 L and about 35 L, or between about 25 L and about 35 L. All combinations of the above bioreactor volumes and working culture volumes are contemplated, providing that the bioreactor volume is greater than or equal to the working volume. For example, in certain embodiments, the cell line is cultured in a 35 L bioreactor culture at a working volume of between about 20 L and about 35 L.

In some embodiments, a cell line of the present disclosure is cultured for at least 7 days, at least 14 days, at least 21 days, at least 28 days, at least 35 days, at least 50 days, or at least 60 days. In some embodiments, a cell line of the present disclosure is cultured for 7 days, 14 days, 21 days, 28 days, 35 days, 50 days, or 60 days. All combinations of the above bioreactor volumes, working culture volumes, and culturing durations are contemplated, providing that the bioreactor volume is greater than or equal to the working volume. In some embodiments, a cell line of the present disclosure is cultured for at least 35 days, at least 50 days, or at least 60 days in a 35 L bioreactor culture. In certain embodiments, a cell line of the present disclosure is cultured for 60 days in a 35 L bioreactor culture. In some embodiments, a cell culture of the present disclosure maintains at least 50%, at least 60%, at least 70%, at least 75%, at least 80%, or at least 85% cell viability after culturing the cell line for 60 days in a 35 L bioreactor culture. In certain embodiments, a cell culture of the present disclosure maintains at least 85% cell viability after culturing the cell line for 60 days in a 35 L bioreactor culture.

In some embodiments, a cell line of the present disclosure is cultured under fed-batch culture conditions. Under fed-batch culturing, one or more compounds or nutrients are added to a cell culture during culturing. After production, the culture is harvested and product recovered.

In some embodiments, a cell line of the present disclosure is cultured under perfusion culture conditions. Under perfusion culturing, fresh culture medium is fed into the culture, and waste/by-products are continuously removed. Perfusion cultures are known to allow for culturing at a greater cell density than fed-batch culturing.

In some embodiments, the methods of the present disclosure further comprise isolating a product, e.g., a recombinant polypeptide and/or viral vector, from a cell line of the present disclosure. Exemplary and non-limiting methods of product isolation and purification are described in greater detail infra.

Techniques for cell culture and recombinant polynucleotide/polypeptide production are described in a non-limiting manner infra.

Selection and Transfection of Host Cells

Host cells can be selected during culturing by various means, including use of the exemplary selectable markers described in section II supra.

Techniques suitable for transfection of human cell lines (e.g., HEK293 cell lines) are known in the art. In some embodiments, HEK293 cells are transfected by introducing DNA into cells using polyethylenimine (PEI). Exemplary methods for PEI transfection of HEK293 cells are described herein and known in the art (see, e.g., www.addgene.org/protocols/transfection/).

Culturing the Host Cells

The host cells of the present disclosure may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source.

Purification of Biologically Active Polypeptide

A recombinant polypeptide (e.g., antibody) composition prepared from the cells can be purified using, for example, hydroxylapatite chromatography, hydrophobic interaction chromatography, gel electrophoresis, dialysis, and affinity chromatography, with affinity chromatography being among one of the typically preferred purification steps. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

In general, various methodologies for preparing antibodies for use in research, testing, and clinical are well-established in the art, consistent with the above-described methodologies and/or as deemed appropriate by one skilled in the art for a particular antibody of interest.

Purification of Viral Vectors

A viral vector prepared from the cells can be purified using various means, depending, e.g., upon the type of viral vector produced. A purified viral vector preparation refers to a preparation of viral vectors/particles devoid of at least some of the other components that may also be present where the particles naturally occur or are initially prepared from. Thus, for example, isolated viral vectors/particles may be prepared using a purification technique to enrich them from a source mixture, such as a culture lysate or production culture supernatant. Enrichment can be measured in a variety of ways, such as, for example, by the proportion of DNase-resistant particles (DRPs) or genome copies (gc) present in a solution, or by infectivity, or it can be measured in relation to a second, potentially interfering substance present in the source mixture, such as contaminants, including production culture contaminants or in-process contaminants, including helper virus, media components, and the like.

Numerous methods are known in the art for production of adenoviral vectors/particles. For example, for a gutted adenoviral vector, the adenoviral vector genome and a helper adenovirus genome can be transfected into a packaging cell line (e.g., a 293 cell line). In some embodiments, the helper adenovirus genome may contain recombination sites flanking its packaging signal, and both genomes may be transfected into a packaging cell line that expresses a recombinase (e.g., the Cre/loxP system may be used), such that the adenoviral vector of interest is packaged more efficiently than the helper adenovirus (see, e.g., Alba, R. et al. (2005) *Gene Ther.* 12 Suppl 1:S18-27). AAV vectors can be generated, e.g., by the triple-plasmid co-transfection of human 293 cells as previously described (Xiao et al. (1998) *J. Virol.* 72:2224-2232). For an exemplary isolation/purification method, AAV vectors can be column purified as previously described (Passini et al., (2001) *J. Virol.* 75:12382-12392).

Numerous methods are known in the art for production of lentiviral vectors/particles. For example, for a third-generation lentiviral vector, a vector containing the lentiviral genome of interest with gag and pol genes may be co-transfected into a packaging cell line (e.g., a 293 cell line) along with a vector containing a rev gene. The lentiviral genome of interest also contains a chimeric LTR that promotes transcription in the absence of Tat (see Dull, T. et al. (1998) *J. Virol.* 72:8463-71). Lentiviral vectors may be harvested and purified using various methods (e.g., Segura M M, et al., (2013) *Expert Opin Biol Ther.* 13(7):987-1011).

Numerous methods are known in the art for production of HSV particles. HSV vectors/particles can be harvested and purified using standard methods. For example, for a replication-defective HSV vector, an HSV genome of interest that lacks all of the immediate early (IE) genes may be transfected into a complementing cell line that provides genes required for virus production, such as ICP4, ICP27, and ICP0 (see, e.g., Samaniego, L. A. et al. (1998) *J. Virol.* 72:3307-20). HSV vectors may be harvested and purified using various methods (e.g., Goins et al., (2014) Herpes Simplex Virus Methods in Molecular Biology 1144:63-79).

EXAMPLES

The disclosure will be more fully understood by reference to the following examples. They should not, however, be construed as limiting the scope of the disclosure. It is understood that the examples and embodiments described herein are for illustrative purposes only and that various modifications or changes in light thereof will be suggested to persons skilled in the art and are to be included within the spirit and purview of this application and scope of the appended claims.

Example 1: Creating and Testing a More Robust HEK293 Cell Line

As noted above, HEK293 cells are sensitive to shear stress and prone to yield low viabilities when cultured in bioreactors. It was hypothesized that a cell line with resistance to apoptosis would exhibit higher productivity and more robust performance in bioreactors. An anti-apoptotic HEK293 cell line (HEK293 DKO) was engineered by deleting the pro-apoptotic genes Bax and Bak using zinc finger nuclease technology (Cost et al. (2010) *Biotechnol. Bioeng.* 105:330-340). During apoptosis, Bax and Bak permeate the mitochondrial membrane which ultimately leads to the activation of caspase proteins that trigger programmed cell death (Taylor et al. (2008) *Nat. Rev. Mol. Cell Biol.* 9:231-241). It was previously shown that deleting Bax and Bak in a CHO cell line correlated with higher culture viabilities and transfection titers (Macaraeg et al. (2013) *Biotechnol. Prog.* 29:1050-1058). Improvements to culture viabilities and productivity have been reported with suppression or deletion of Bax and Bak (Cost et al. (2010) *Biotechnol. Bioeng.* 105: 330-340; Lim et al. (2006) *Metab. Eng.* 8:509-522; Gray et al. (2015) *Biotechnol. J.* 10:1446-1456). These studies reported observing higher viability (Cost et al. (2010) *Biotechnol. Bioeng.* 105:330-340; Macaraeg et al. (2013) *Biotechnol. Prog.* 29:1050-1058; Lim et al. (2006) *Metab. Eng.* 8:509-522), higher DNA uptake levels (Macaraeg et al. (2013) *Biotechnol. Prog.* 29:1050-1058), higher transfection efficiency (Macaraeg et al. (2013) *Biotechnol. Prog.* 29:1050-1058), greater mitochondria mass (Misaghi et al. (2013) *Biotechnol. Prog.* 29:727-737), and improved mitochondria membrane potential (Misaghi et al. (2013) *Biotehcnol. Prog.* 29:727-737) in CHO DKO production cultures compared to wild-type.

The HEK293 DKO was tested and characterized in order to create a HEK293 cell line that exhibits higher productivity and robust performance in bioreactors.

Methods

Cell Culture

The HEK293 DKO cell line was created by using zinc finger nuclease technology (Cost et al. (2010) *Biotechnol. Bioeng.* 105:330-340). HEK293 cells and HEK293 DKO cells were cultivated as a seed train in shake flasks as previously described (Bos et al. (2015) *Biotechnol. Bioeng.* 112:1832-1842) using the seed train media in Table 1.

TABLE 1

Seed train and production media used for HEK293 and HEK293 DKO transient transfections.

| Cell type | Seed train medium | Production medium |
|---|---|---|
| HEK293 | Expi293 Expression Medium (ThermoFisher, Cat# A1435101) | HyCell TransFX-H Medium (GE, Cat# SH30939) |
| HEK293 DKO | HyCell TransFX-H Medium (GE, Cat# SH30939) | HyCell TransFX-H Medium (GE, Cat# SH30939) |

Staurosporine Assay

HEK293 and HEK293 DKO seed train cultures in shake flasks were seeded at 0.8×10⁶ cells/mL and either untreated or treated with 1 µM staurosporine (Sigma, Cat #S6942). Cultures were sampled every day for viability.

Flow Constriction Device (FCD)

An FCD (Mollet et al. (2007) *Biotechnol. Bioeng.* 98:772-788) was used to assess the impact of shear stress on HEK293 and HEK293 DKO cells. Briefly, a syringe pump (Harvard Apparatus, Model #33) was used to pass the cells through the FCD at a flow rate of 70 mL/min or an energy dissipation rate (EDR) of 2.67×10⁷ W/m³. Before passing through the FCD, whole cell samples (positive controls) were diluted 1:1 with 0.2 g/L saponin (Amresco, Cat #0163) in water to lyse the cells and stored at −80° C. After passing through the FCD, the cultures were centrifuged at 830×g and the supernatants were diluted 1:1 with 0.2 g/L saponin and stored at −80° C. The samples were thawed and assayed for lactate dehydrogenase (LDH) using a Cedex Bio HT Analyzer (Roche). Total lysis after FCD (%) was calculated using equation 1 below. Cultures were also sampled for viable cell density (VCD) and viability before and after passing through the FCD.

$$\text{Total Lysis After } FCD\ (\%) = \frac{LDH \text{ of sample after } FCD}{LDH \text{ of whole cell}} \times 100 \quad (1)$$

Transfection

Transient transfections were performed at a 30 mL working volume in 50 mL tubespins or 125 mL shake flasks, at a 10 L working volume in a 22 L wavebag, or at a 12 mL working volume in ambr15 microbioreactors.

For 30 mL transfections, cells were seeded at 2×10⁶ cells/mL in 25.5 mL of production medium (see Table 1) in a 50 mL tubespin (Optimum Processing, Cat #SV92050) or 125 mL nonbaffled shake flask (Corning, Cat #431143) and equilibrated for 2 hours prior to transfection at 37° C., 5% CO₂ in a shaking incubator at 225 rpm with a 50 mm orbital diameter (Kuhner, Model #ISF1-X) or at 125 rpm with a 25 mm orbital diameter (e.g., Kuhner, Innova), respectively. All transfections were performed using a DNA encoding a standard human IgG1 (huIgG1) antibody. To transfect, indicated amounts of DNA and 25 kDa linear PEI at 7.5 mM (Polyplus-transfection, Cat #101) were incubated in 3 mL of serum-free media (e.g., Opti-MEM I Reduced-Serum Medium (ThermoFisher, Cat #31985062)) for 15 minutes before addition to the equilibrated cells. A 2.6 mL solution containing hydrolysates, amino acids and salts, and glucose was added 24 hours post-transfection. This process was scaled proportionally for smaller or larger working volumes.

Cell Count, Titer, and Product Quality Measurements

Cultures were sampled every 1-4 days for viable cell densities (VCDs), viability, metabolites, pH, and/or gases and were measured using a Vi-CELL Cell Counter (Beckman Coulter), a BioProfile FLEX Analyzer (Nova Biomedical), or an ABL90 FLEX (Radiometer). HuIgG1 antibody titers from supernatant samples were determined using a Protein A HPLC assay. HuIgG1 antibody product quality attributes including level of aggregation, acidic and basic variants, and various glycoforms were determined using size exclusion HPLC, imaged capillary isoelectric focusing (icIEF), and hydrophilic interaction liquid chromatography (HILIC) HPLC, respectively.

N:P Experiments

Transfections were performed as described above. To determine the conditions that produce the highest titer, a full factorial experiment tested PEI:DNA (N:P) ratios of 5, 7.5, 10, and 12.5 and DNA concentrations of 0.75, 1.0, 1.25, and 1.5 µg/mL. An N:P ratio of 7.5 and a DNA concentration of 1 µg/mL yielded the highest titers (FIG. 2A) and, therefore, was used for all subsequent transfections. 2 L and 35 L bioreactor seed trains HEK293 DKO cells were cultivated as a seed train in two controlled 2 L bioreactors (Applikon) for 25 days. Bioreactor #1 used a pH setpoint of 7.0 with a deadband of ±0.03 and a DO setpoint of 30% air saturation and bioreactor #2 used a pH setpoint of 7.0 with a deadband of ±0.4 and a DO setpoint of 60% air saturation. Culture pH was controlled using CO₂ as acid and 1 M sodium carbonate as base, and DO was controlled by sparging with air and pure oxygen gas via an open pipe sparger. Temperature was maintained at a setpoint of 37° C., and a pitched blade impeller was used to agitate at 275 rpm.

Subsequently, HEK293 DKO cells were cultivated as a seed train in a 35 L bioreactor (Chemglass) for 60 days using a pH setpoint of 7.0 with a deadband of ±0.03 and a DO setpoint of 30% air saturation. Culture pH and DO were controlled the same as in the 2 L bioreactors. Temperature was maintained at a setpoint of 37° C. and a flat blade impeller was used to agitate at 50 rpm.

Ambr15 Microbioreactor System

Transfections were performed in the ambr15 microbioreactor system (Sartorius Stedim Biotech; see Hsu, W. T. et al. (2012) *Cytotechnology* 64:667-678) as described above with a 12 mL final working volume, a temperature setpoint of 37° C., and a DO setpoint of 30% air saturation. The full factorial experiment of 4 cases in replicate evaluated agitation rates of 630 vs 1400 rpm using a pitched blade impeller and pH deadbands of ±0.03 vs ±0.3 around a setpoint of 7.0. Culture pH was controlled using $CO_2$ as acid and 0.5 M sodium carbonate as base, and DO was controlled by sparging with air and pure oxygen gas via a sparge tube. Every 1-2 days, antifoam (Dow Corning) was added to each ambr15 bioreactor.

Wavebag Bioreactor System

The wavebag bioreactor system consisted of a heated, rocking platform (GE Healthcare, Model #20/50EHT), a gas mix box (Dasgip, Model #MX4/4), and a 22 L nominal volume wavebag (e.g., Thermo or Meissner; custom items) with inlet and outlet gas filters and a sampling port. Transfections were performed as described above with a 10 L final working volume, a temperature setpoint of 37° C., a rock rate of 20 rpm, a rock angle of 8°, and no direct pH control with a gas overlay of 5% CO2 in air at a flow rate of 27 standard liters per hour (slph).

Results

The susceptibility of the HEK293 DKO cell line to undergo apoptosis and its sensitivity to shear stress were tested. To induce apoptosis, staurosporine was added to HEK293 and HEK293 DKO cultures. Upon staurosporine addition, HEK293 DKO cells maintained higher viability compared to HEK293 cells (FIG. 1A). From this, it was inferred that the HEK293 DKO cells are more resistant to apoptosis.

Figure 1B:
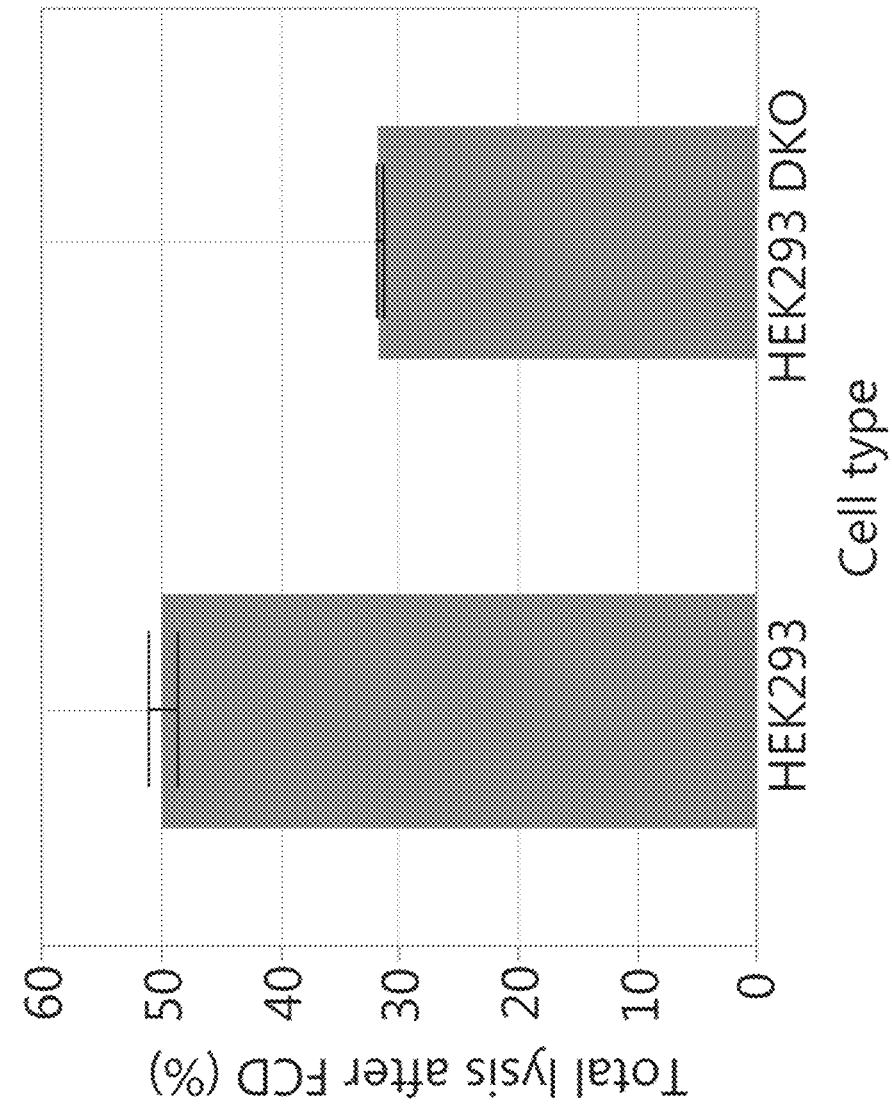
Figure 1C:
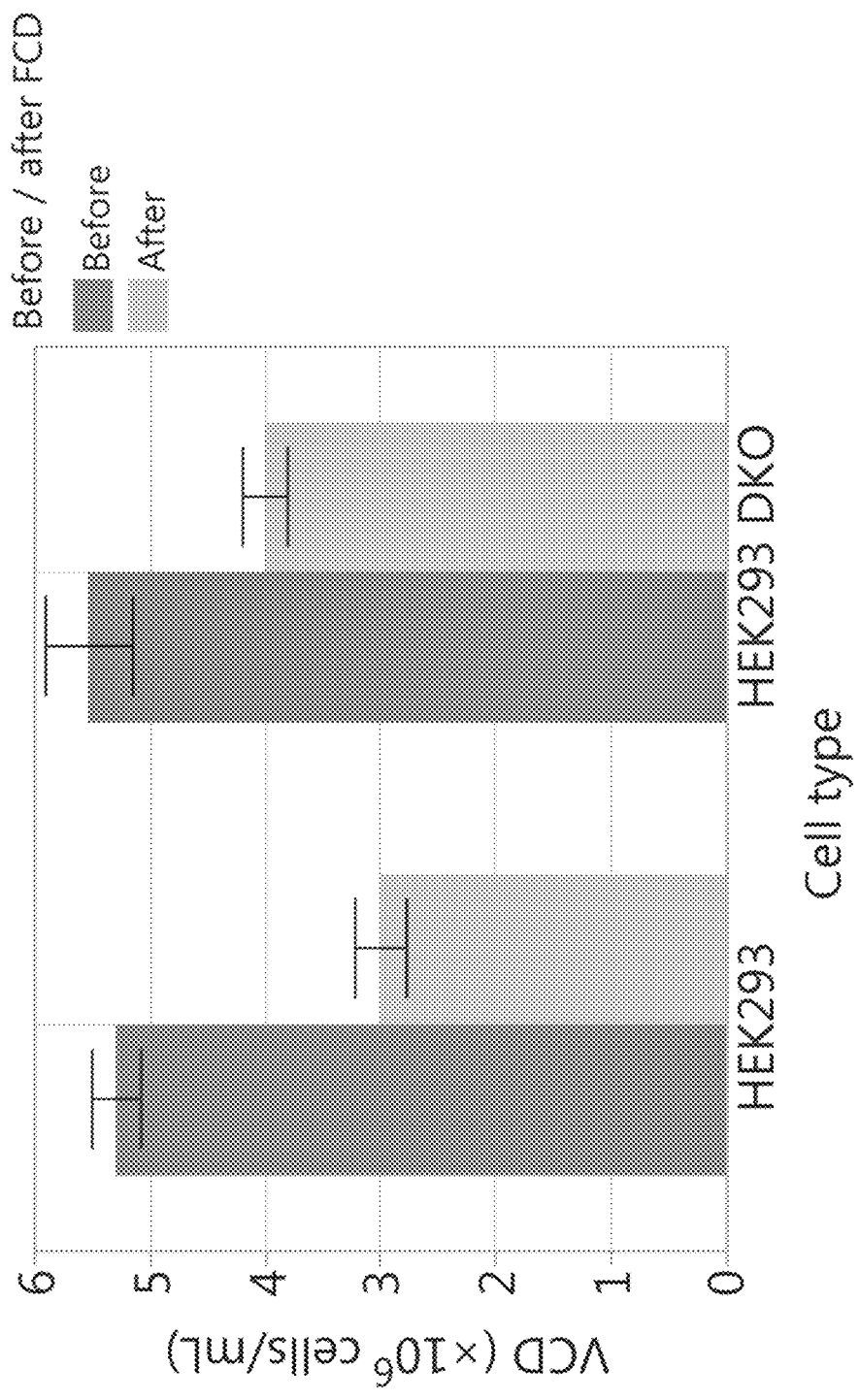
Figure 1D:
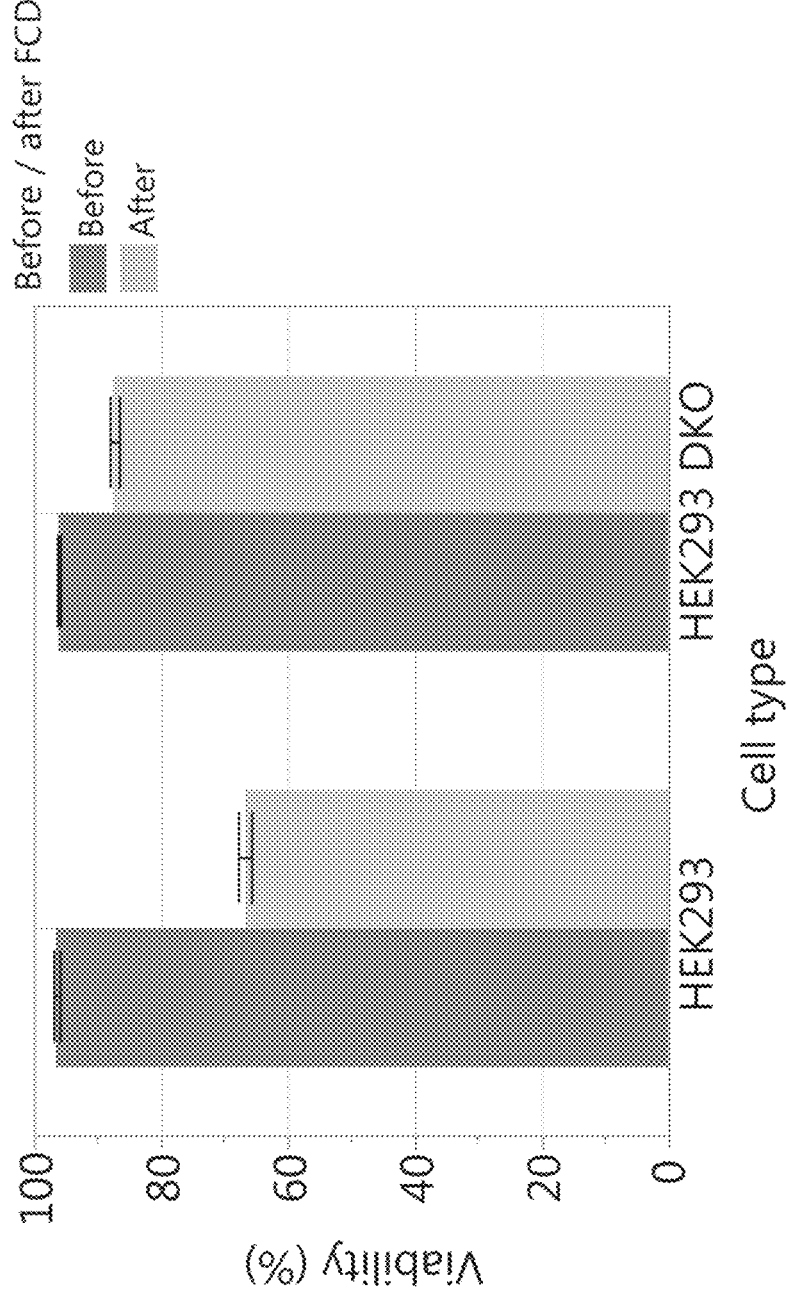

To assess the impact of shear stress, HEK293 and HEK293 DKO cultures were passed through a flow constriction device (FCD; Ma et al. (2002) *Biotechnol. Bioeng.* 75:197-203; Mollet et al. (2007) *Biotechnol. Bioeng.* 98:772-788). The FCD subjected cells to an acute hydrodynamic force and increased shear stress equivalent to a $2.67 \times 10^7$ W/m$^3$ energy dissipation rate (EDR) by passing the cells at a controlled flow rate through a narrow flow channel. After flowing through the FCD, the HEK293 DKO cells exhibited higher cell densities, higher viability, and reduced lysis compared to HEK293 cells (FIGS. 1B-1D), indicating that HEK293 DKO cells are more resistant to shear stress than HEK293 cells. Thus, the HEK293 DKO cell line demonstrates the desired phenotypic properties through the deletion of Bax and Bak.

Figure 2A:
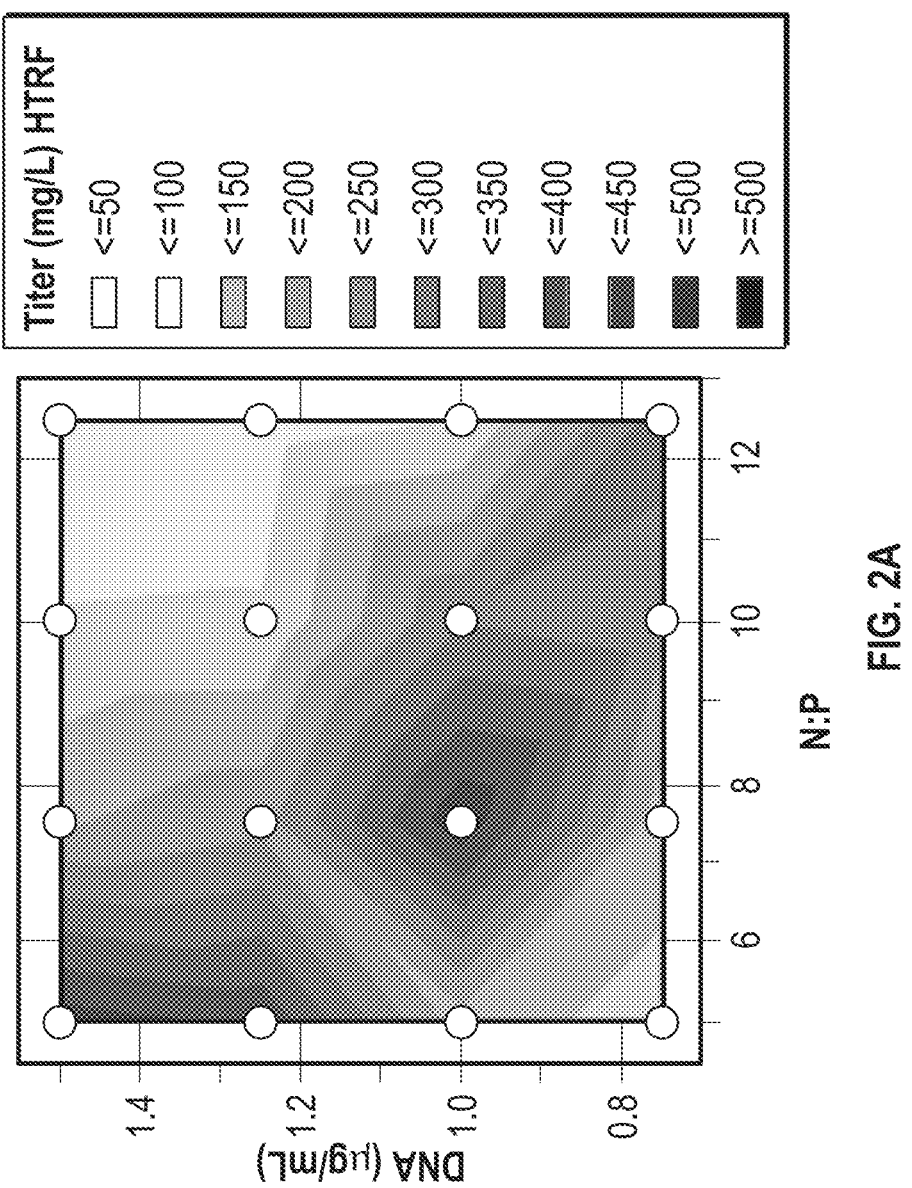
FIGS. 2A-2C show the optimization of N:P ratio and DNA concentration for HEK293 DKO transient transfections. Transfections were tested across N:P ratios of 5 to 12.5 and DNA concentrations of 0.75 to 1.5 µg/mL (FIG. 2A).

The ratio of PEI (N) to DNA (P) and the amount of PEI and DNA can significantly impact transient transfection productivity (Delafosse et al. (2016) *J. Biotechnol.* 227:103-111; Macaraeg et al. (2013) *Biotechnol. Prog.* 29:1050-1058; Choosakoonkriang et al. (2003) *Journal of Pharmaceutical Sciences* 92:1710-1722; Bertschinger et al. (2008) *Mol. Biotechnol.* 40:136-143). To determine the HEK293 DKO transient transfection conditions that produce the highest titer, 30 mL tubespin production cultures were seeded at $2 \times 10^6$ cells/mL, and a full factorial experiment was run to test a range of N:P ratios (5, 7.5, 10, and 12.5) and DNA concentrations (0.75, 1.0, 1.25, and 1.5 μg/mL). A N:P ratio of 7.5 and DNA concentration of 1 μg/mL yielded the highest titers (FIG. 2A).

Figure 2B:
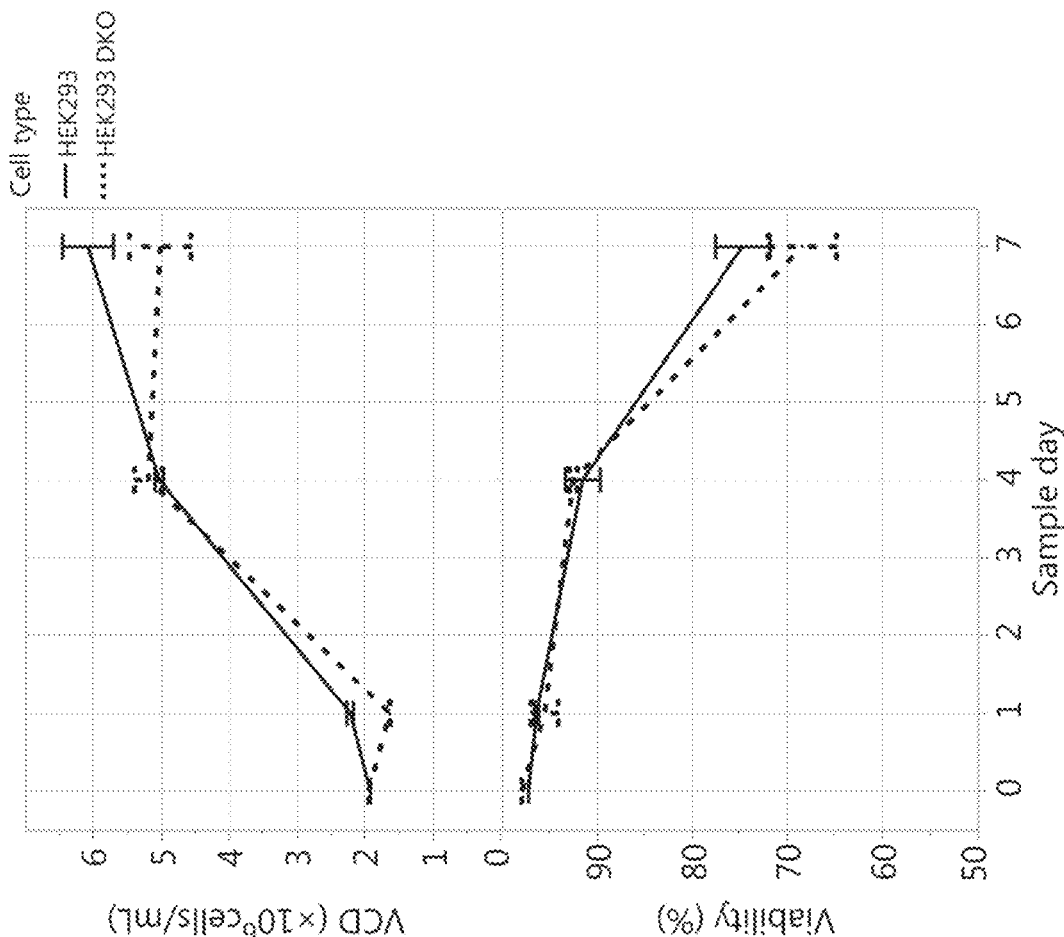
Figure 2C:
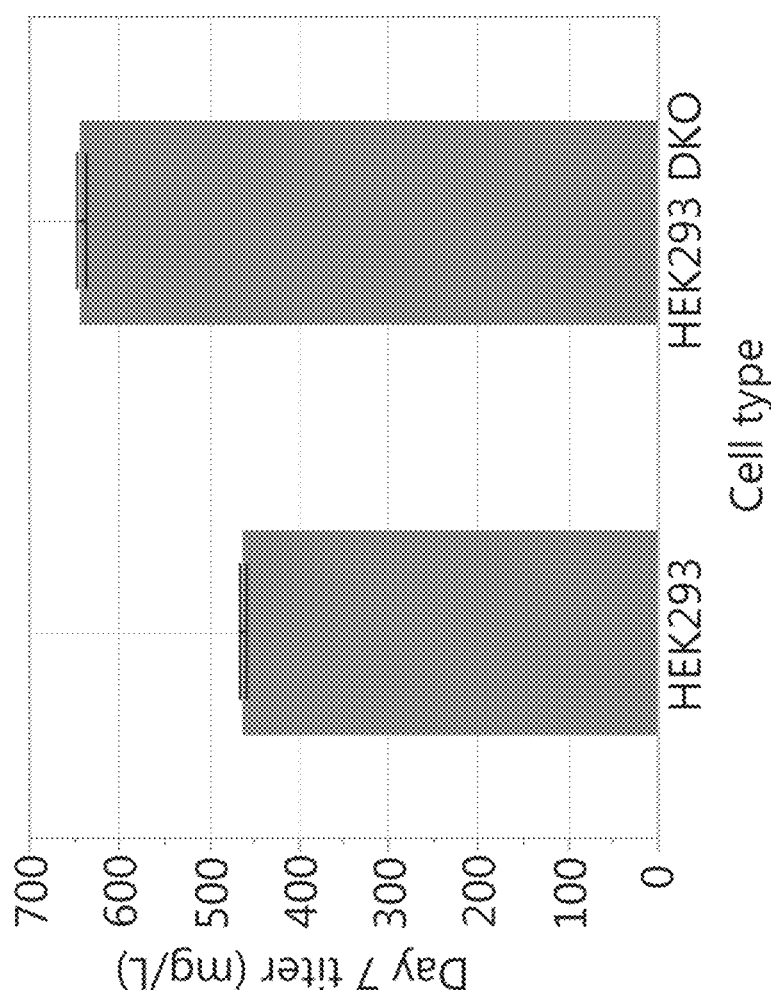

Using this optimized condition, HEK293 DKO transient transfection performance was compared to the HEK293 in 30 mL tubespins. Both cell types showed similar growth and viability in transfection, with final day viabilities at 68.5% and 74.9% for HEK293 DKO and HEK293 cultures, respectively (FIG. 2B). This suggests that the viability decline in these transfection cultures is induced by necrosis rather than apoptosis. With regards to productivity, the HEK293 DKO cultures expressed 40% higher titer than HEK293 cultures (FIG. 2C). Without wishing to be bound to theory, it is thought that the difference in productivity could be due to sublethal effect of shear stress on HEK293 cultures, or biological effects of deleting Bax and Bak. The optimized N:P ratio of 7.5 and DNA concentration of 1 μg/mL were used for all further HEK293 DKO transfections with the 30 mL scale as the control for scale up/down.

In summary, the HEK293 DKO cell line was more resistant to apoptosis and shear stress than the HEK293 parental cell line. This property renders the HEK293 DKO cell line advantageous for high throughput transient production of recombinant proteins and potentially other HEK293 applications such as stable production of biopharmaceuticals, viral vectors, and vaccines.

Example 2: Scaling Up the HEK293 Seed Train

To efficiently generate cell mass to support large scale (10 L) transfections, the HEK293 DKO seed train was cultivated in a 35 L controlled bioreactor rather than multiple shake flasks. A regularly passaged (i.e. split every 3-4 days) seed train bioreactor with a working volume of 20-35 L would provide enough cells to start 40-70 L of transfections seeded at $2 \times 10^6$ cells/mL twice per week. This enables routine execution of high throughput, large scale transient production runs.

Before testing the HEK293 DKO seed train in a 35 L bioreactor, different pH and dissolved oxygen (DO) controlled conditions were first evaluated in two 2 L bioreactors. Bioreactor #1 used a pH setpoint of 7.0 with a deadband of ±0.03 and a DO setpoint of 30%; these are typical conditions for CHO stable cell line cultures (Li et al. (2010) *mAbs.* 2:466-477; Li et al. (2012) *Biotechnol. Bioeng.* 109:1173-1186; Yuk et al. (2011) *Biotechnology Progress* 27:1397-1406). Bioreactor #2 used a pH setpoint of 7.0 with a deadband of ±0.4 and a DO setpoint of 60% to more closely trend with the pH and DO conditions of a shake flask. HEK293 DKO cells were passaged in a shake flask and the 2 L bioreactors in parallel, every 3-4 days for a total of 25 days and monitored growth and metabolites.

Figure 3A:
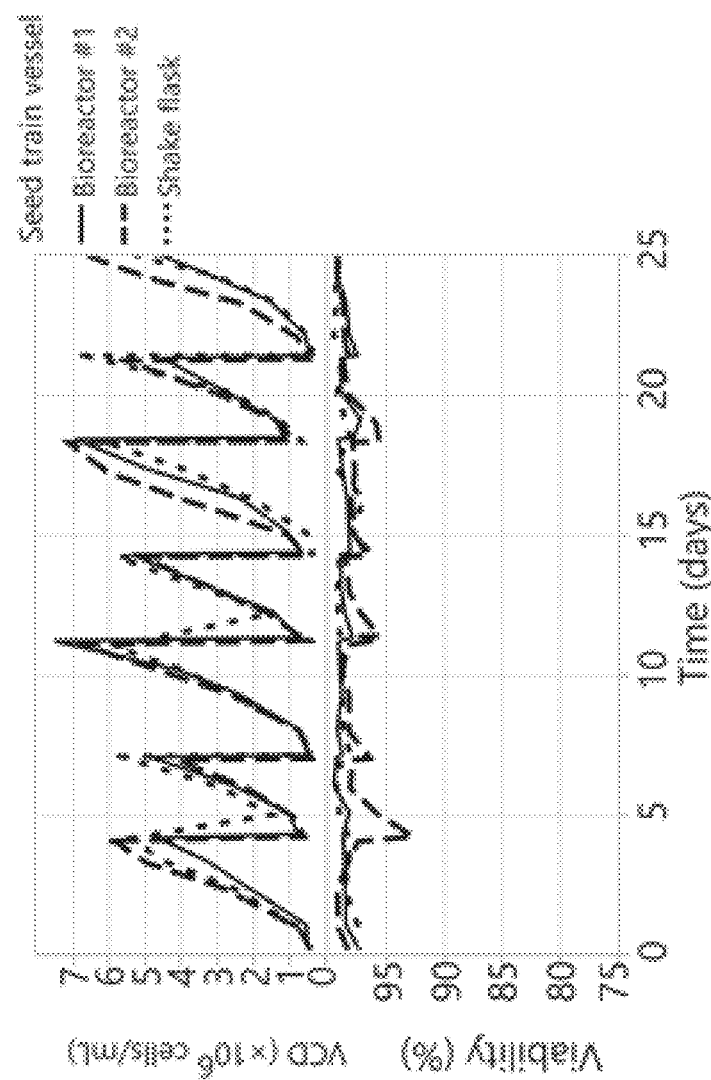
FIGS. 3A-3E show the effect of scaling up the HEK293 DKO seed train from a 1 L shake flask to controlled 2 L bioreactors. Bioreactor #1: pH setpoint of 7 with a deadband of ±0.03 and a DO setpoint of 30%. Bioreactor #2: pH setpoint of 7 with a deadband of ±0.4 and a DO setpoint of 60%. Passaging the 1 L shake flask and 2 L bioreactors every 3-4 days for 25 days.
Figure 3B:
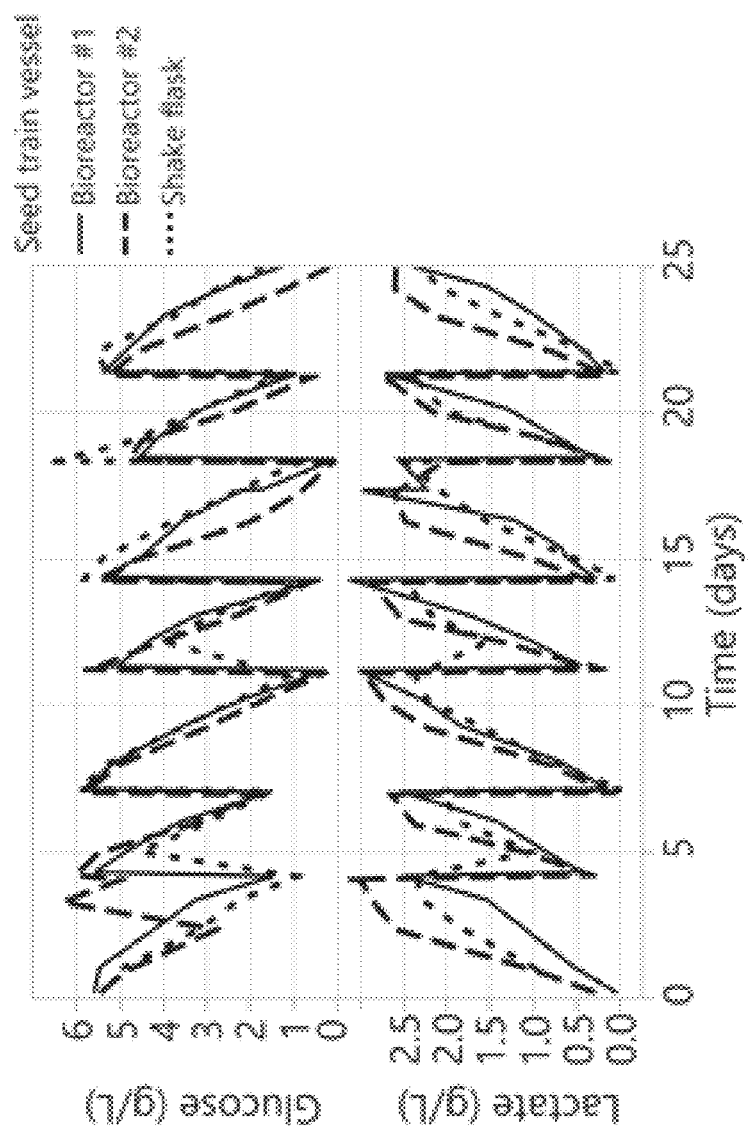
Figures 3C, 3D:
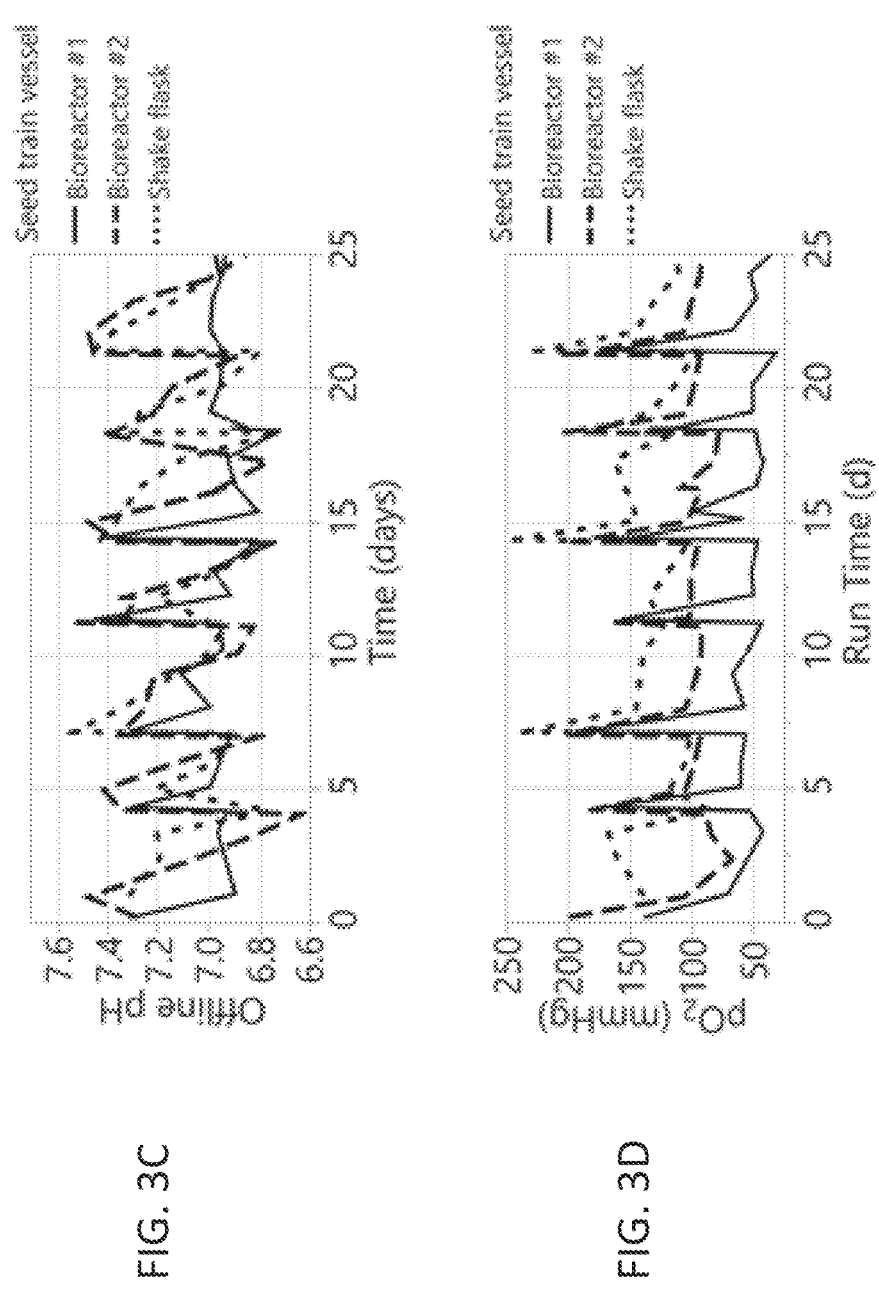
Figure 3E:
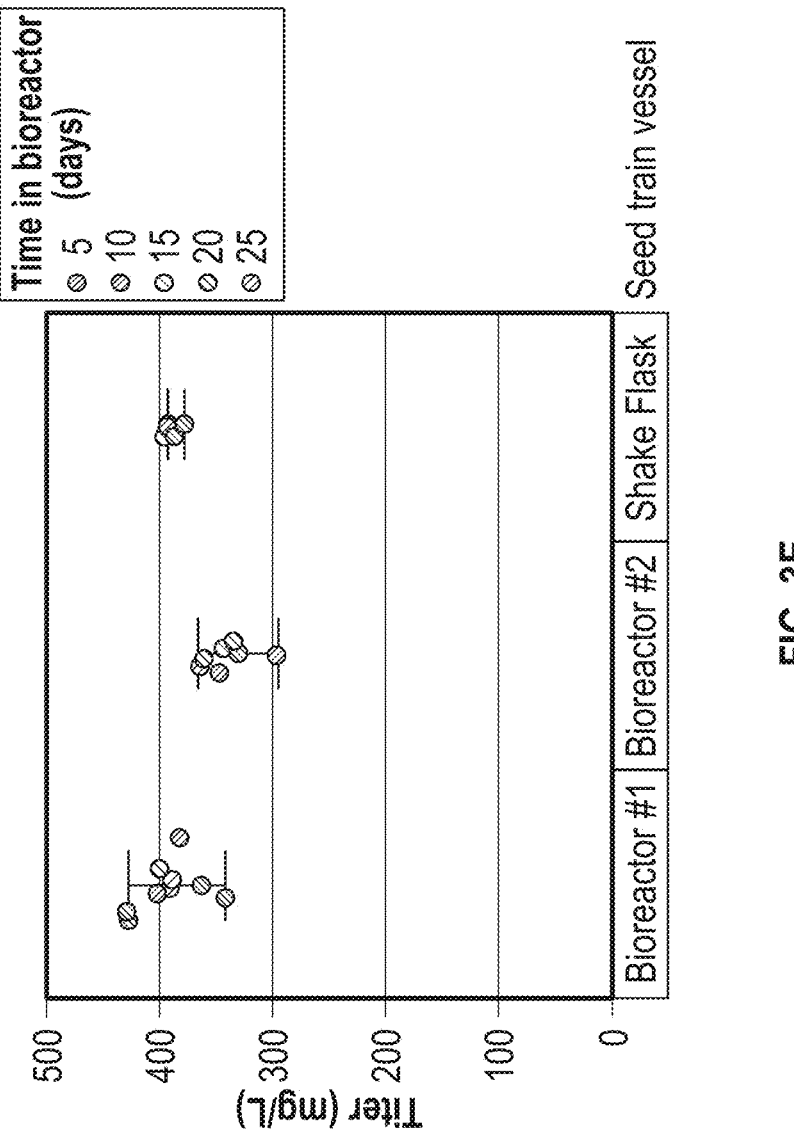

Both 2 L bioreactor HEK293 DKO seed trains grew to similar peak cell densities and maintained similar viabilities compared to the shake flask seed train (FIG. 3A). This correlates with similar glucose consumption and lactate production across the seed trains (FIG. 3B). Bioreactor #2 showed similar pH and DO trends to the shake flask (FIGS. 3C&3D). Cells from the seed trains were used every week for 4 weeks in 30 mL tubespin transfections. Interestingly, modestly lower titers were observed from cells sourced from bioreactor #2 that mimicked the shake flask pH and DO conditions and similar titers from cells sourced from bioreactor #1 with tighter controls (FIG. 3E) compared to titers from cells sourced from the shake flask seed train. Different mixing in the shake flask seed train may account for the cells' high productivity. In the bioreactor, it is possible that the narrow pH deadband conditions impacted the seed train cells and/or their spent medium such that they were more amenable for transfection. This could entail biological modifications that (1) result in more optimal electrostatic charge interactions of the DNA/PEI complex with the cell surface during transient transfection, (2) promote intracellular trafficking of DNA/PEI complexes to the nucleus, or (3) enhance transcription, translation, and secretion of the recombinant protein.

Subsequently, the HEK293 DKO seed train was scaled up to a 35 L bioreactor using bioreactor #1 conditions (pH setpoint of 7.0 with a narrow deadband of ±0.03 and DO setpoint of 30%) and matching the power input per volume of our 2 L bioreactor (13 W/m$^3$). The HEK293 DKO shake flask and 35 L bioreactor seed trains were passaged in parallel every 3-4 days for a total of 60 days and monitored regularly for growth and metabolites. While the HEK293 DKO cells showed comparable transfection productivity for up to 150 days after thaw, a 60 day duration was chosen for the bioreactor to balance the frequency of bioreactor breakdown/set up—a labor intensive operation—with ensuring that cellular debris on the glass wall of the bioreactor at the liquid-air interface does not accumulate from continuous passaging in the bioreactor. This contrasts with the shake flask seed train procedure in which a new shake flask was used for every passage.

Figure 4A:
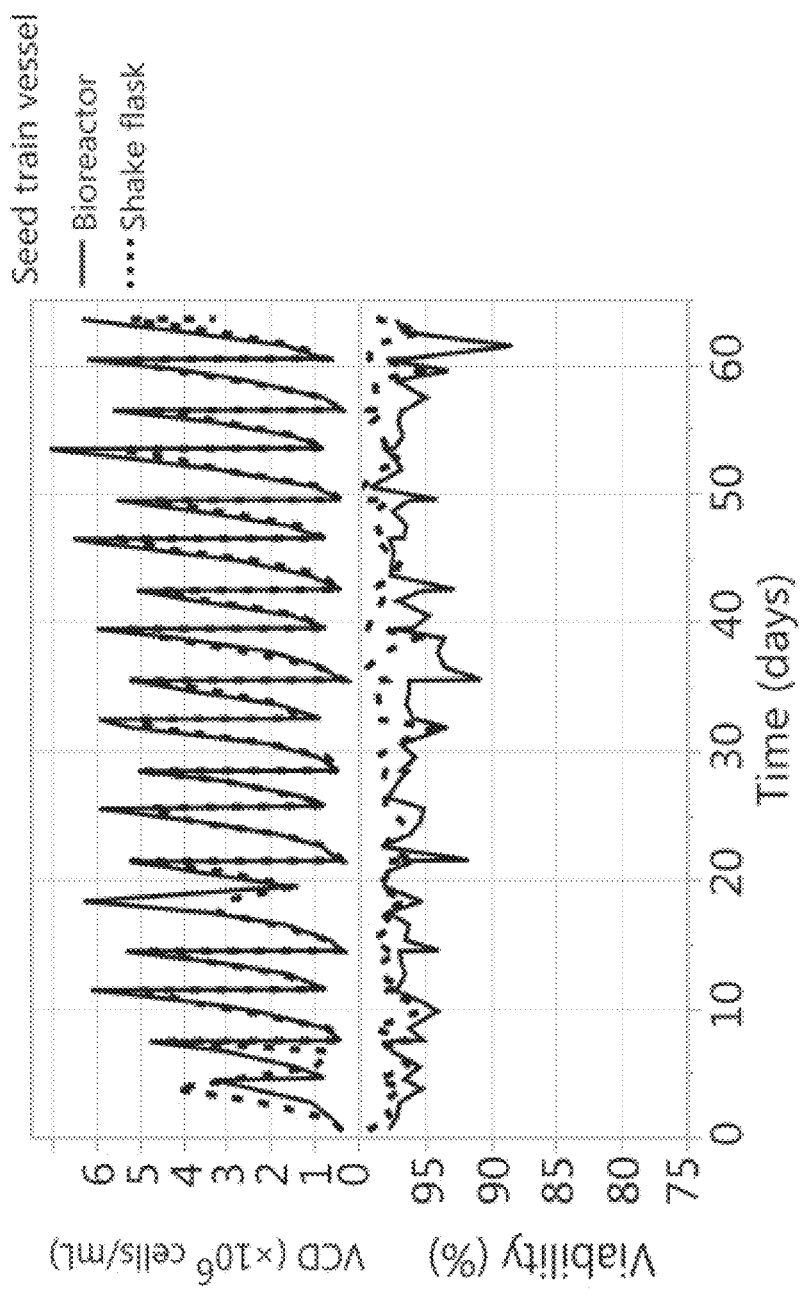
FIGS. 4A-4D show the scale-up of the HEK293 DKO seed train from a 1 L shake flask to a controlled 35 L bioreactor. Passaging the 1 L shake flask and 35 L bioreactor every 3-4 days for 60 days.
Figure 4B:
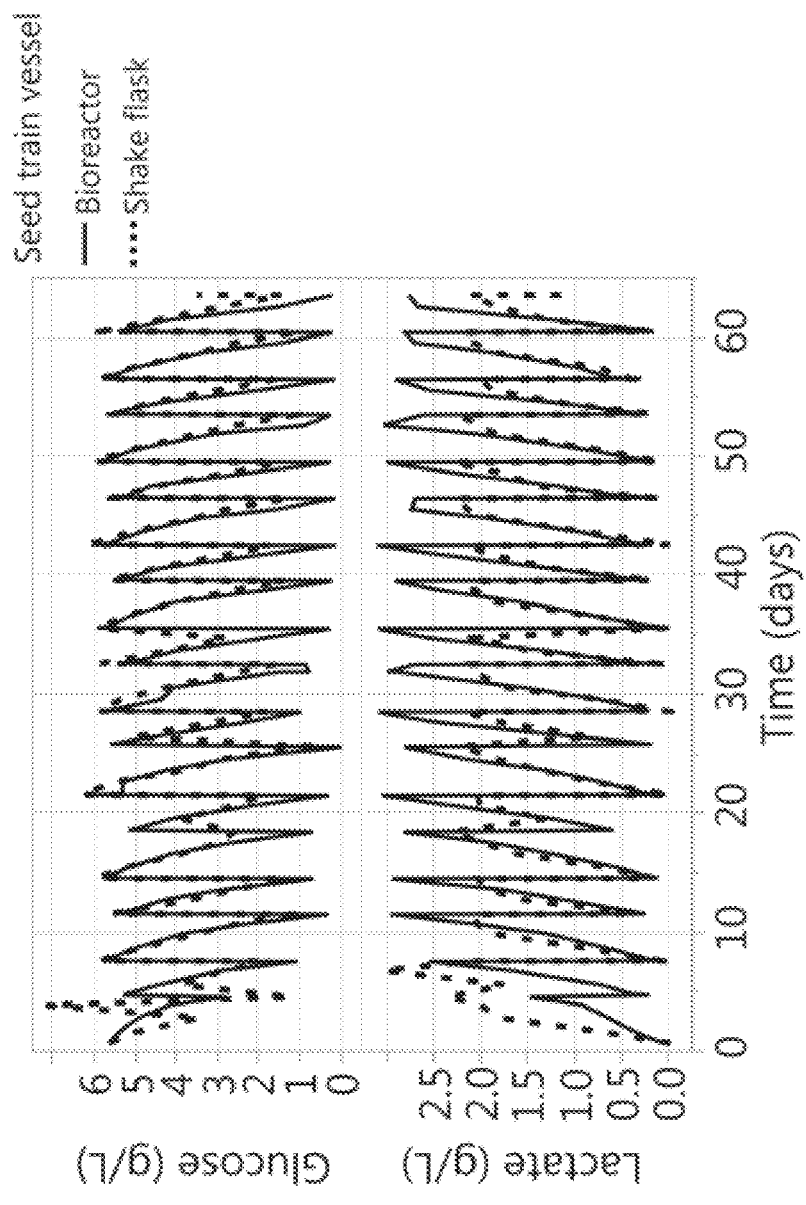
Figure 4C:
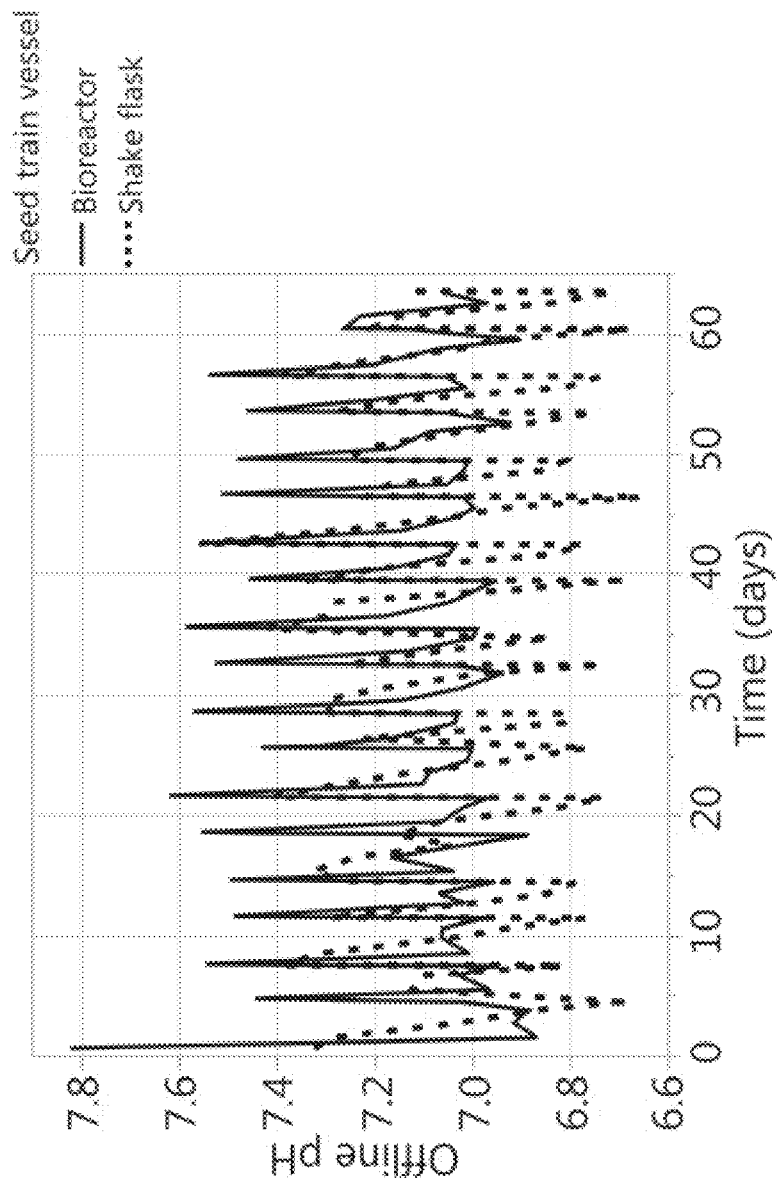
Figure 4D:
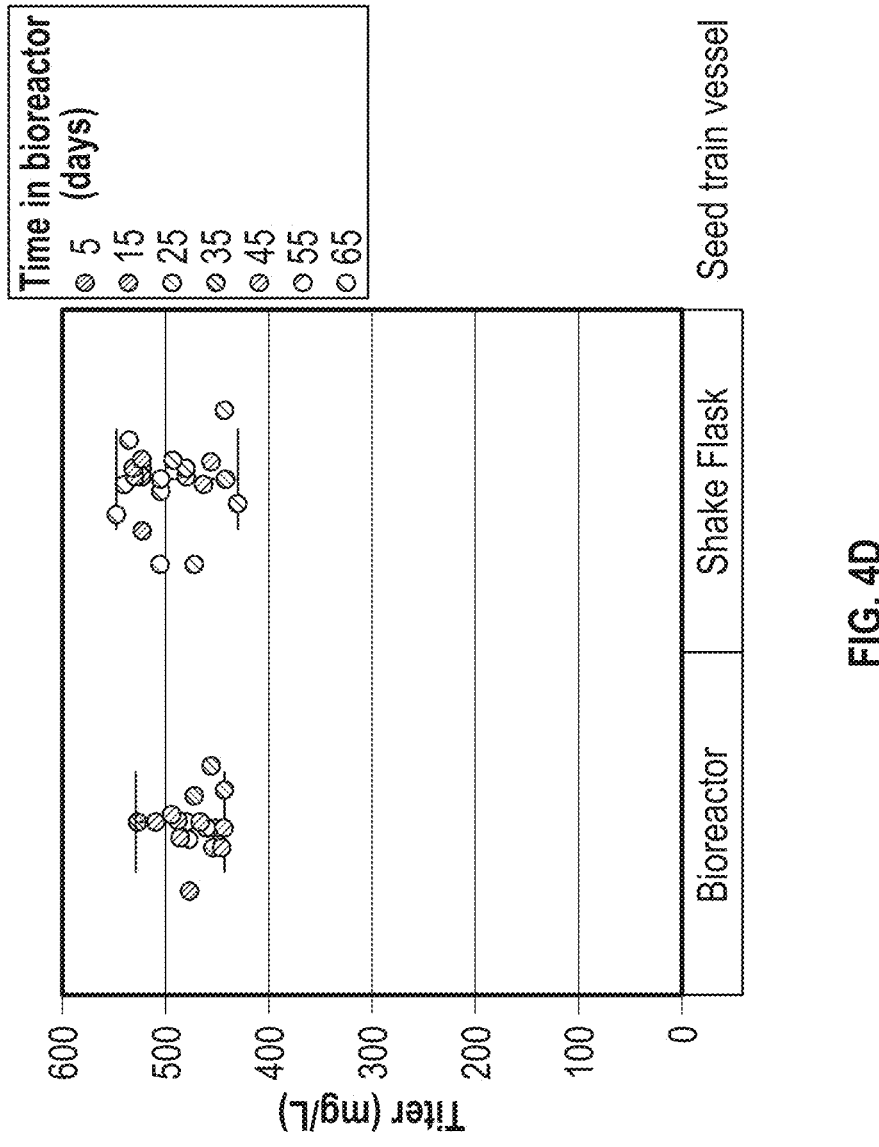
Figure 4E:
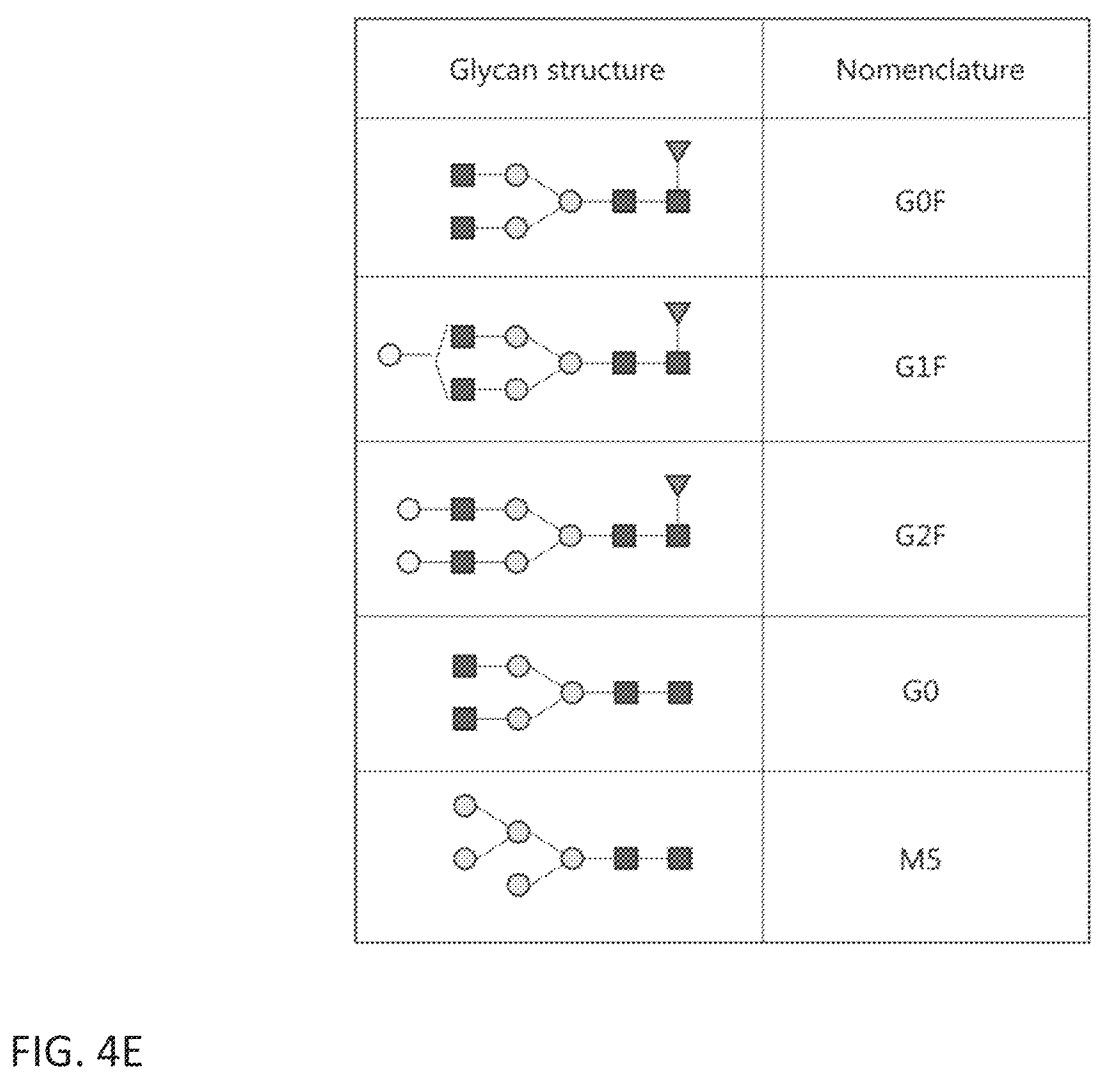
Figure 4F:
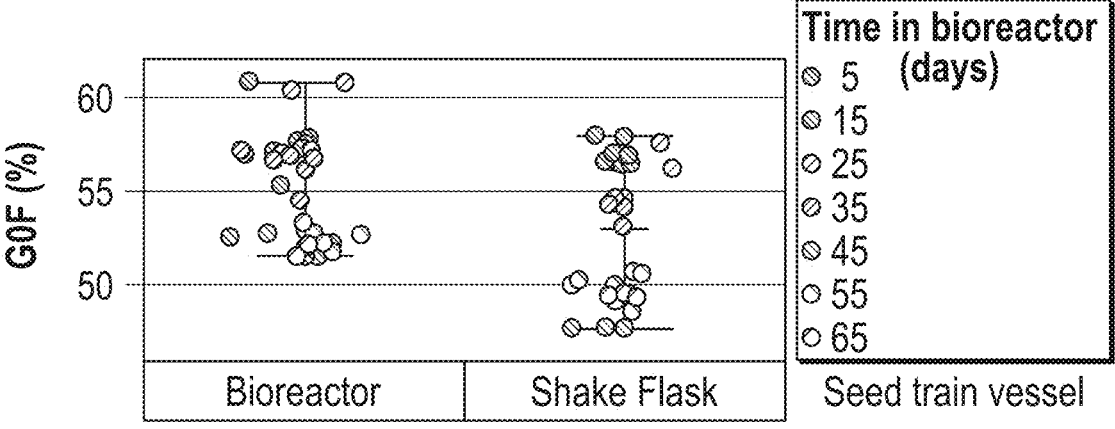
Figure 4G:
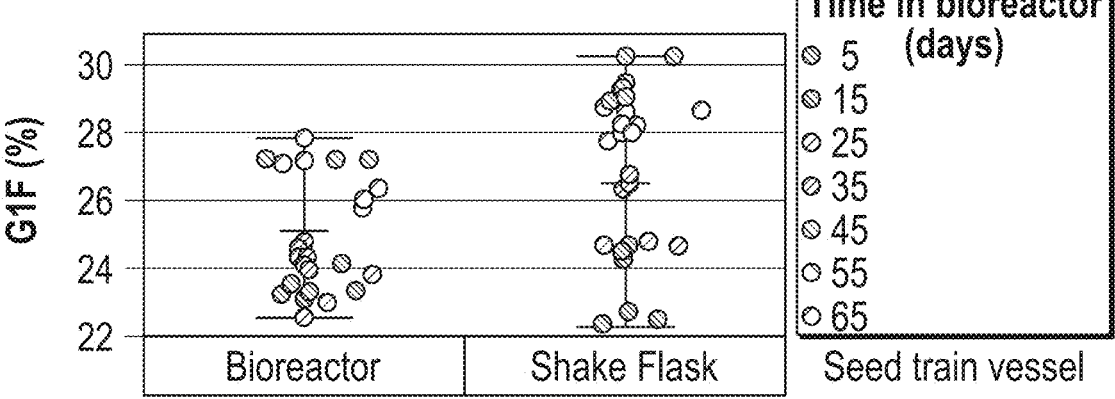
Figure 4H:
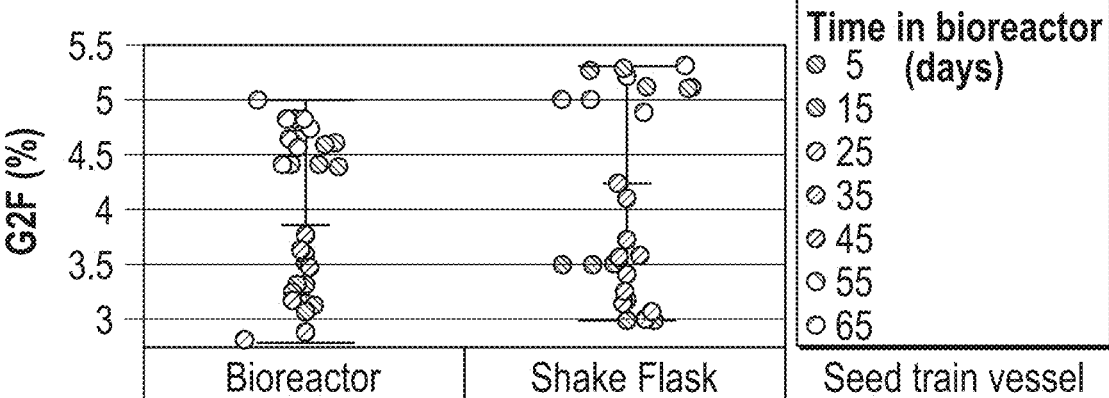
Figure 4I:
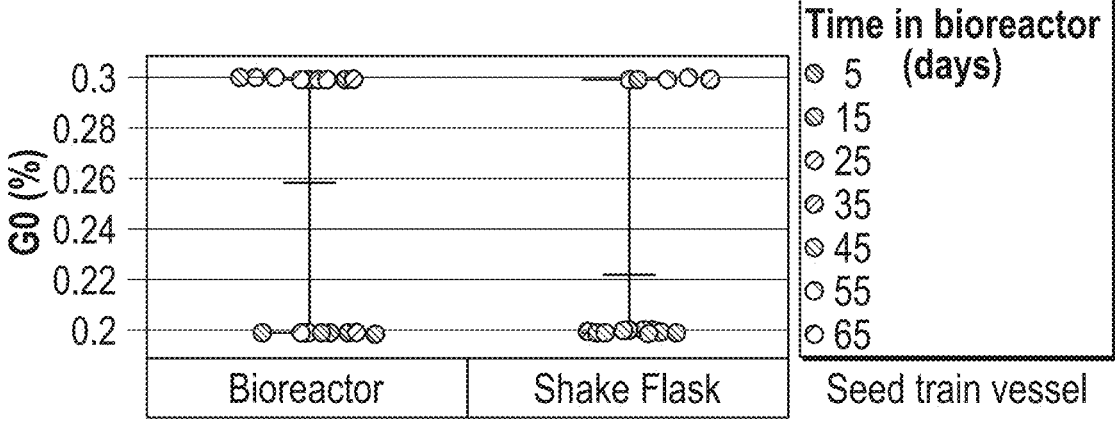
Figure 4J:
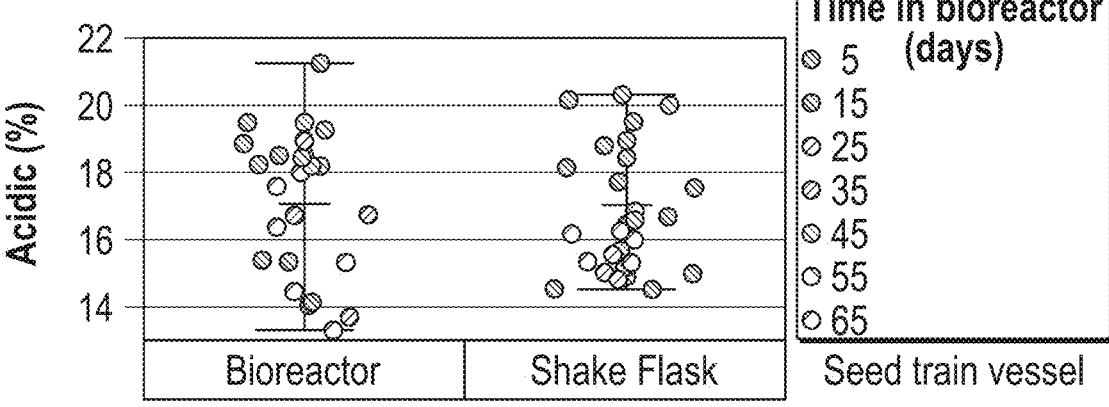
Figure 4K:
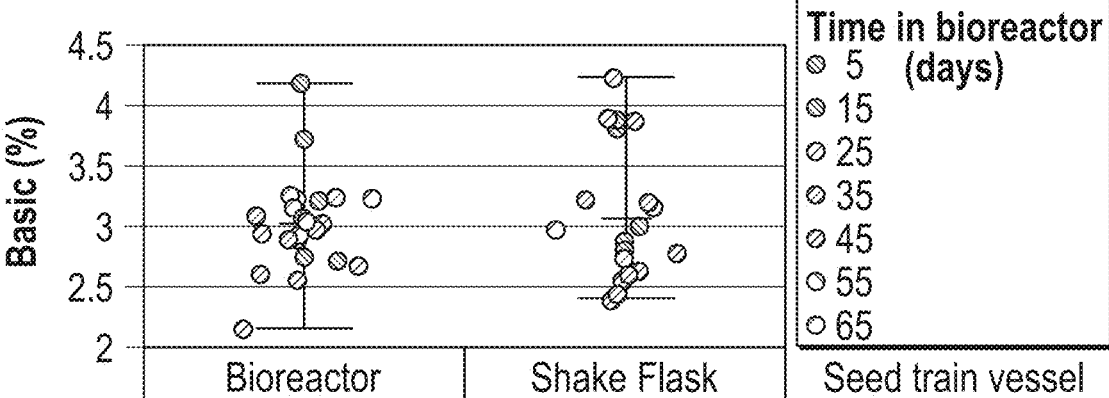
Figure 4L:
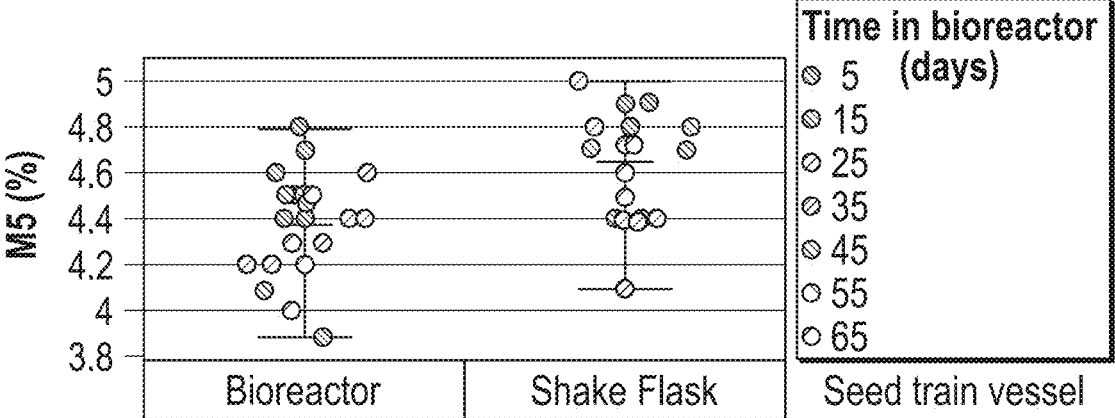
Figure 4M:
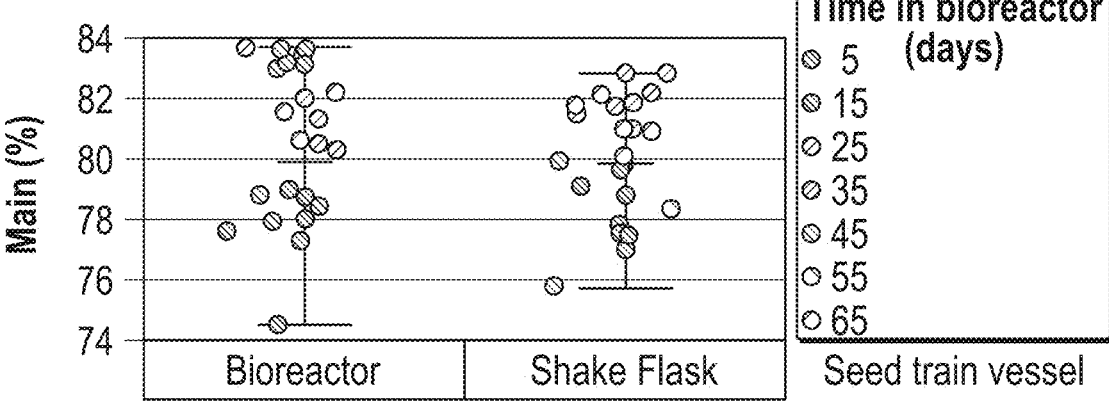
Figure 4N:
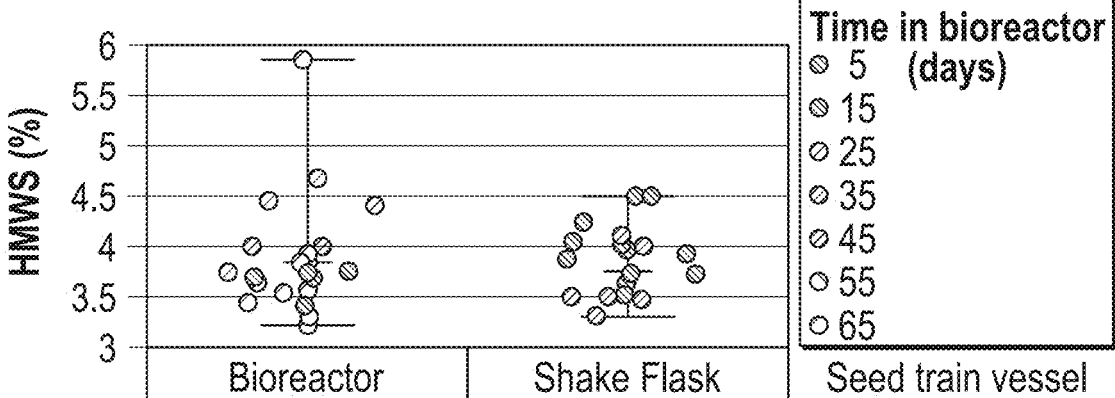

The bioreactor HEK293 DKO seed train achieved slightly higher peak cell densities and lower viabilities compared to the shake flask seed train (FIG. 4A). As expected, due to pH control, the bioreactor seed train consumed more glucose and produced more lactate than the shake flask (FIG. 4B). This glucose consumption differs from the 2 L bioreactor seed trains (FIG. 3B) and may be due to scale differences including sparging and mixing. Except for pH spikes during passaging of the bioreactor, the bioreactor seed train maintained its pH at 7.0 with a deadband of ±0.03 (FIG. 4C). The bioreactor maintained its DO setpoint of 30% with similar trends to the analogous 2 L bioreactor. Every week for 9 weeks, cells from the seed trains were used for 30 mL tubespin transfections. Despite the differences noted above between the bioreactor and shake flask seed train, cells sourced from the shake flask and 35 L bioreactor produced similar titers (FIG. 4D) and product quality (FIGS. 4E-4N) across 9 weeks of transfection. The HEK293 DKO cell line exhibited robust performance in a seed train bioreactor. The bioreactor seed trains grew to peak cell densities that enable using ≤50% seed train culture to seed the production culture (at 2×10$^6$ cells/mL), which minimizes the volume of spent media in production. Carry over of >50% spent media with the seed train into production was shown to negatively impact transient protein expression (Tuvesson et al. (2008) *Cytotechnol.* 56:123-136).

These data demonstrate that the HEK293 DKO seed train can be cultivated in a 35 L bioreactor up to 60 days to source weekly transfections. This is the first report that describes long term cultivation of HEK293 seed train at pilot scale (35 L) in a stirred tank, controlled bioreactor. While there is a report of the cultivation of HEK293 cells in a 1.8 L bioreactor for 10 days (Liste-Calleja et al. (2015) *Appl. Microbiol. Biotechnol.* 99:9951-9960), the seed train strategy demonstrated herein supports 35 L of culture for up to 60 days to supply routine, high throughput large scale transient transfections.

Numerous manuscripts describe the achievement of high titers from transfections seeded at high densities (Rajendra et al. (2015) *Biotechnol. Bioeng.* 112:977-986; Backliwal et al. (2008) *Biotechnol. Bioeng.* 99:721-727; Rajendra et al. (2011) *J. Biotechnol.* 153:22-26; Blaha et al. (2015) *Protein Expr. Purif.* 109:7-13; Sun et al. (2008) *Biotechnol. Bioeng.* 99:108-116; Jain et al. (2017) *Protein Expr. Purif.* 134:38-46). However, in these reports, production cultures were seeded or diluted multiple times on different days and relied on centrifugation and medium exchange to obtain high culture densities. This differs from the transfection process described herein in which production cultures were only seeded on the day of transfection by diluting the seed train culture with medium, an approach more conducive to high throughput operations.

Example 3: Optimizing and Scaling Up HEK293 Transfections and Production

Ambr15 bioreactors have been used for CHO stable cell line process development (Wales and Lewis (2010) *Bioprocessing J.* 9:22-25). However, at present, there are no reports describing the optimization of transfection production conditions for HEK293 cultures in ambr15 bioreactors.

To identify optimal parameters and assess feasibility of transfecting HEK293 DKO cells in controlled bioreactors, transfections were performed in ambr15 microbioreactors at varying agitation and pH conditions as described above. The full factorial experiment of 4 cases in replicate evaluated agitation rates of 630 vs 1400 and pH deadbands of ±0.03 vs ±0.3 around a setpoint of 7.0. High and low agitations were selected based on 2 scale up/down strategies (Hsu, W. T. et al. (2012) *Cytotechnology* 64:667-678): (1) 630 rpm matches the power input per volume (P/V) of the 2 L bioreactor (13 W/m$^3$) and (2) 1400 rpm matches the maximum shear (represented by impeller tip speed) of the 2 L bioreactor (0.26 m/s). The pH deadbands were chosen to mimic bioreactor and shake flask conditions. Transfected cultures were monitored for growth and metabolites. Because of equipment limitations, 30 mL shake flasks were used instead of tubespins for the control cases.

Figure 5A:
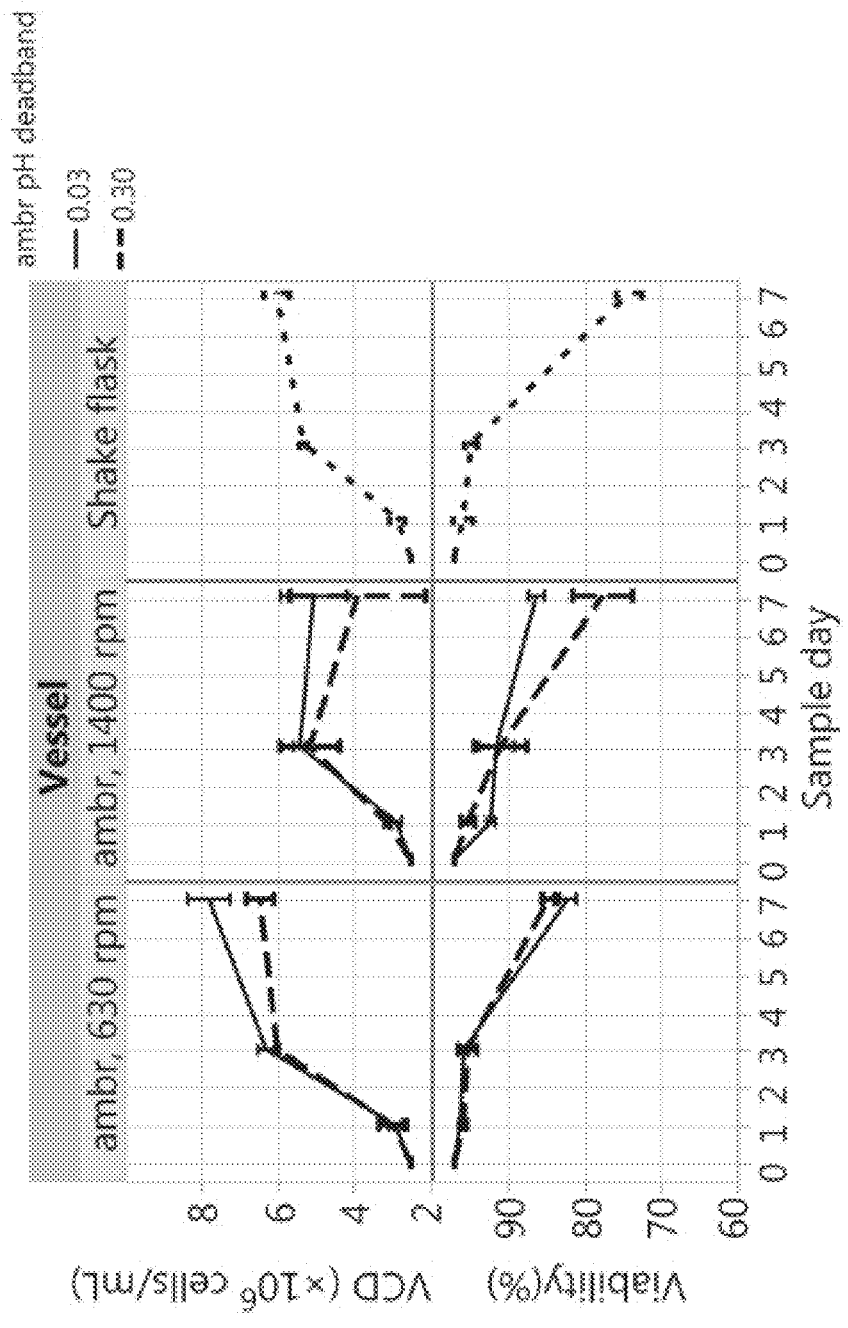
FIGS. 5A-5E show the results of HEK293 DKO transient transfections in controlled ambr15 bioreactors compared to 30 mL shake flasks.
Figure 5B:
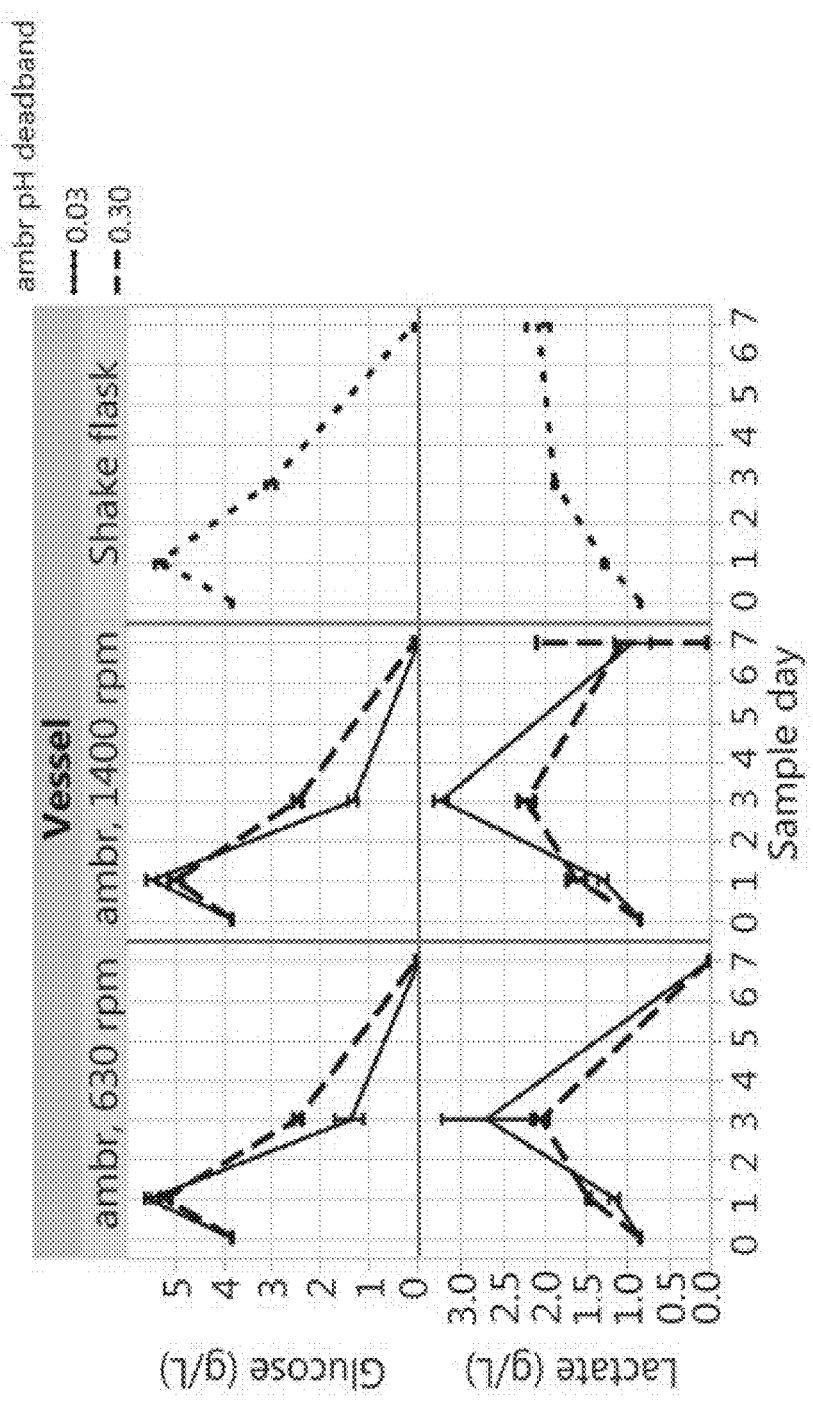
Figure 5C:
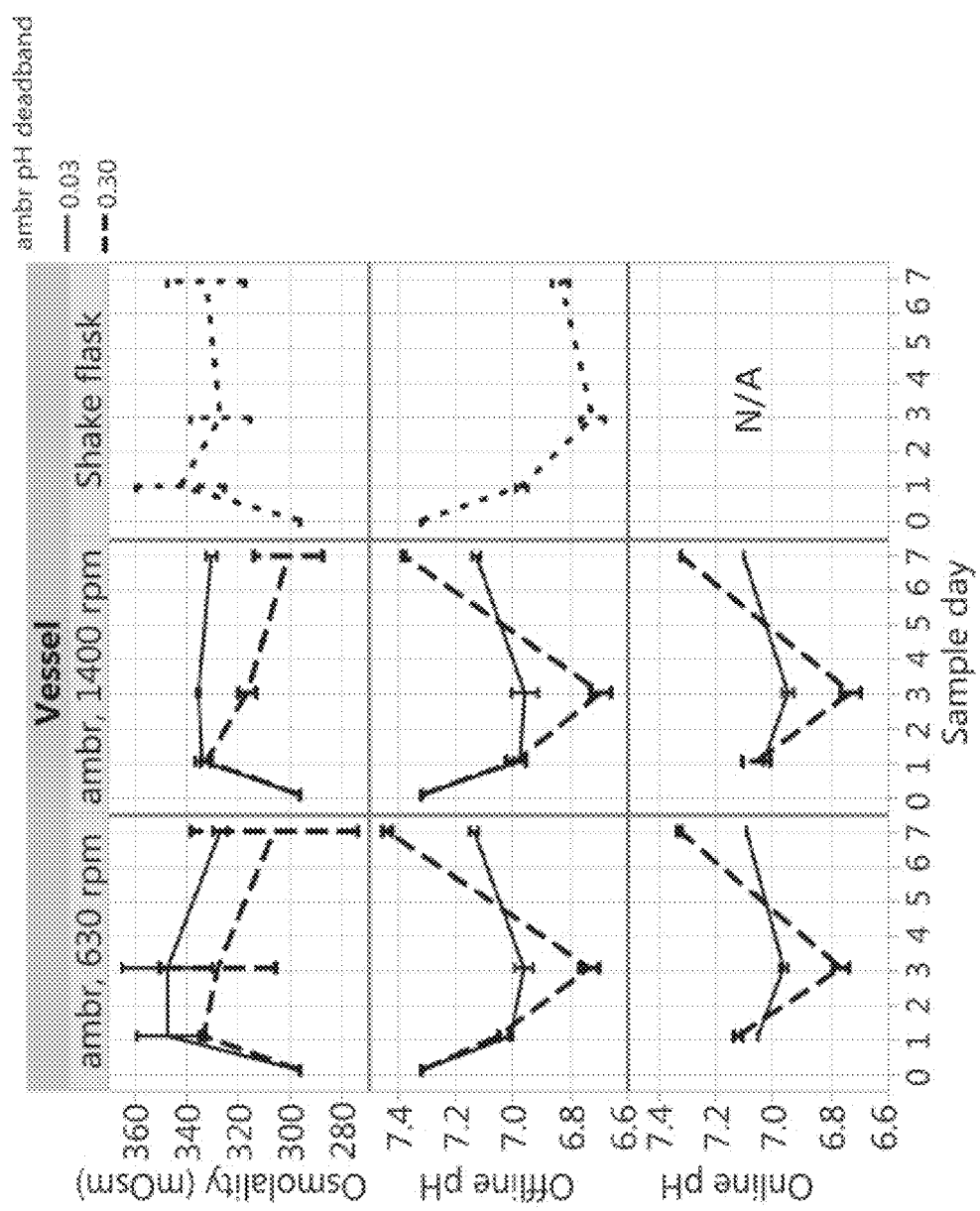
Figures 5D, 5E:
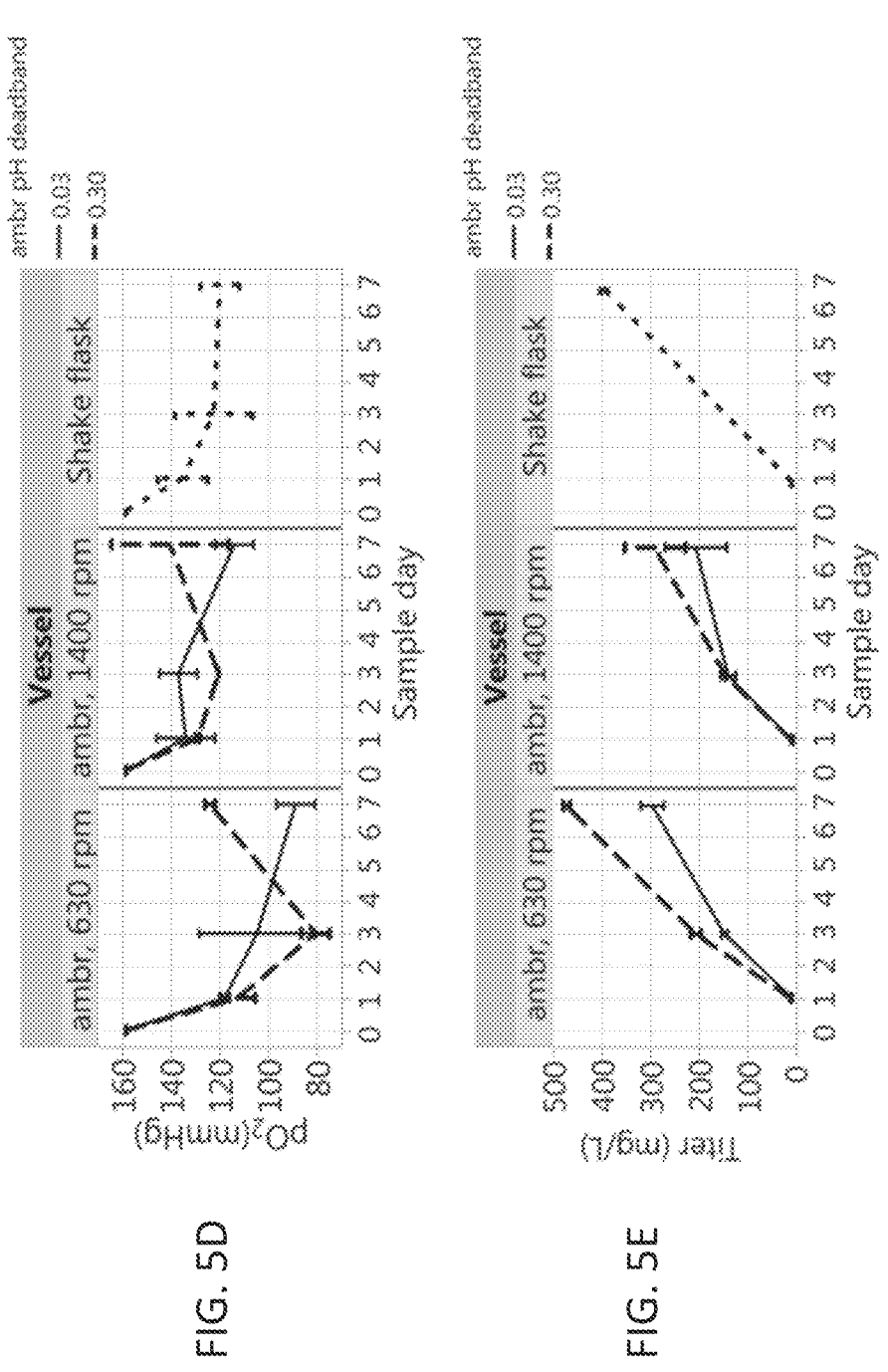

Shake flasks and tubespins produced comparable titers at the 30 mL scale (data not shown). Higher viable cell density and viability correlated with ambr agitation at 630 rpm and pH control around a tight ±0.03 pH deadband (FIG. 5A). Despite similar glucose consumption across all vessels, the ambr bioreactor cultures had lower final lactate levels compared to shake flask cultures (FIG. 5B) indicating that the metabolism of HEK293 DKO cells was different with pH control—lactate was consumed near the end of production. The wide pH deadband of ±0.3 correlated with lower osmolality levels due to fewer base additions and showed similar pH trends to shake flask cultures (FIG. 5C). As expected, oxygen levels were highest and most similar to shake flasks with an ambr agitation of 1400 rpm (FIG. 5D). Highest yields occurred in ambr bioreactors at an agitation of 630 rpm and a wide pH deadband of ±0.30 (FIG. 5E). Without wishing to be bound to theory, it is thought that these higher titers may be due to (1) lower levels of shear stress at 630 rpm allowing for more optimal interaction of DNA/PEI complexes with cells during transfection or more conducive conditions for protein expression, and (2) a wide ±0.3 pH deadband leading to reduced base additions to maintain the pH near the end of production, which directly correlates with lower osmolality and lower final lactate.

Next, knowing that a wide ±0.3 pH deadband correlated with high yields in ambr bioreactors, the transfection of HEK293 DKO cells was scaled up and evaluated without direct pH control in 10 L wavebags and 30 mL tubespins. The wavebags and tubespins were operated without direct pH control with a gas overlay of 5% $CO_2$ in air. The transfected cultures were monitored for growth and metabolites.

Figure 6A:
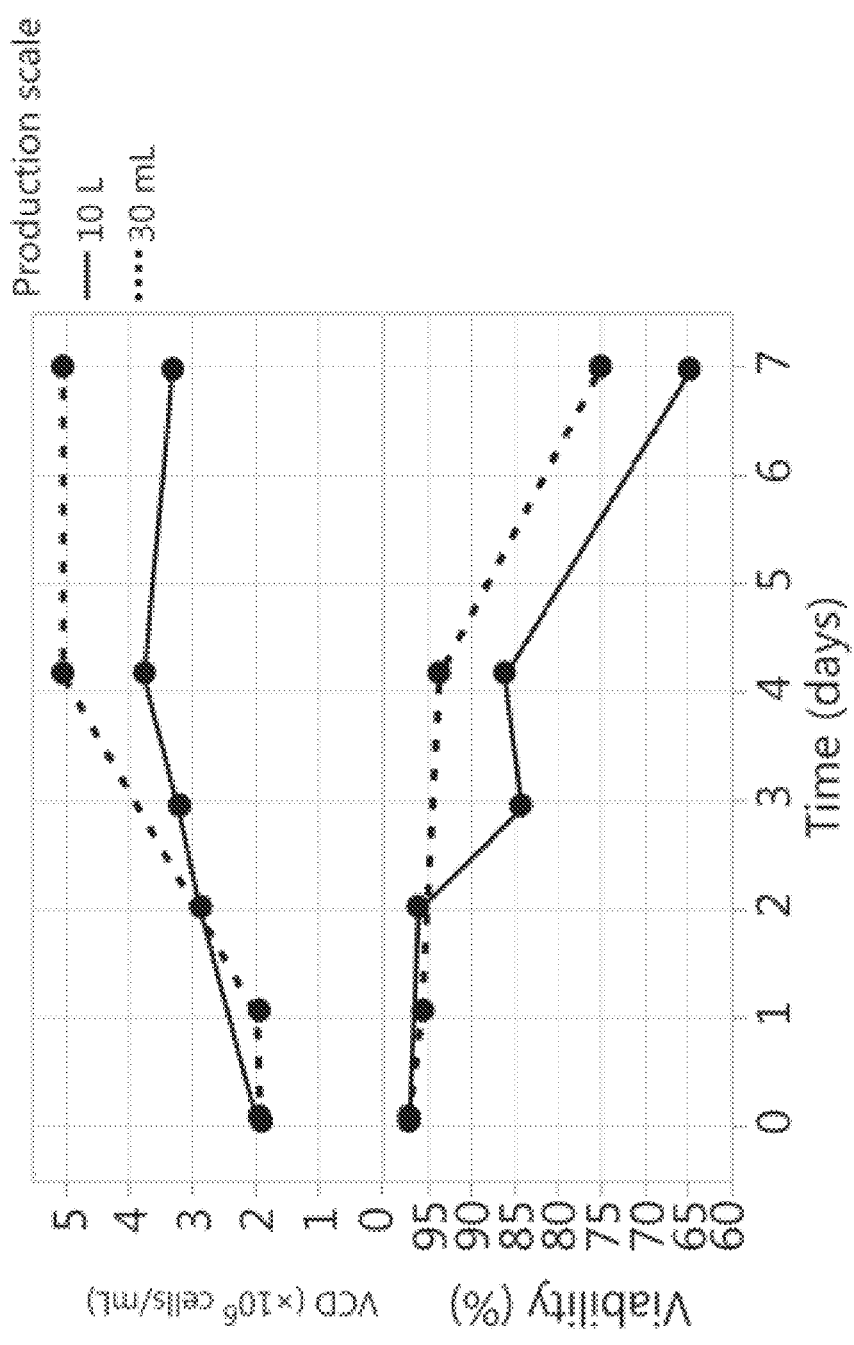
FIGS. 6A-6E show the results of scaling up HEK293 DKO transient transfections from a 30 mL tubespin to a 10 L wavebag.
Figure 6B:
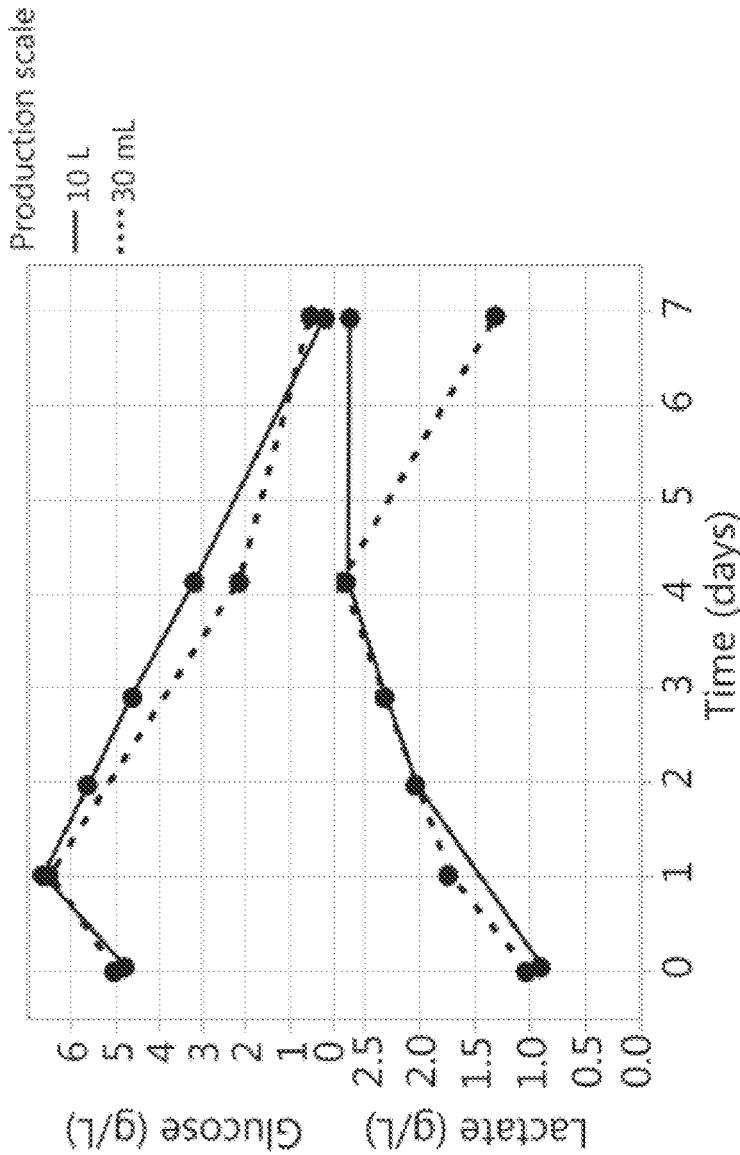
Figure 6C:
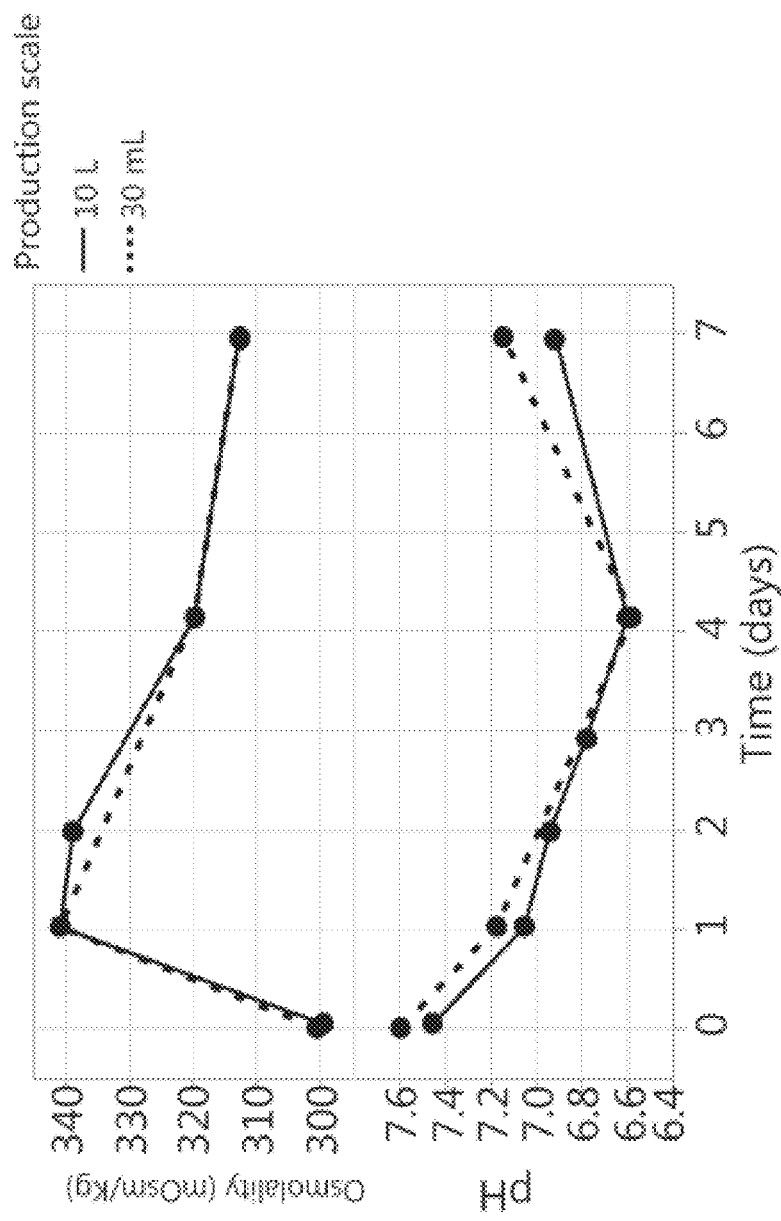
Figures 6D, 6E:
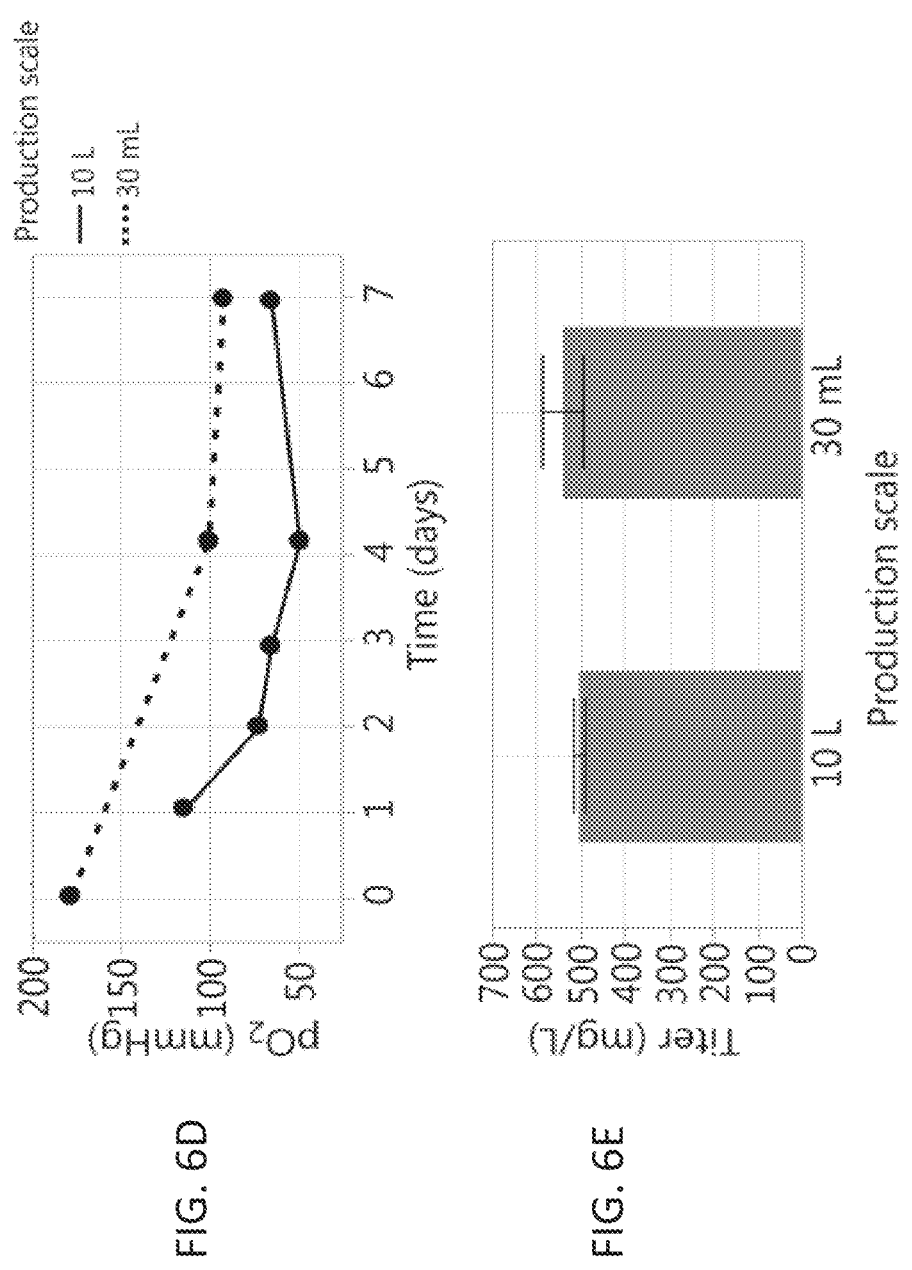

The transfected cells in the 30 mL tubespin reached a higher cell density with higher final viability compared to the 10 L wavebag (FIG. 6A). However, these cell counts may have been confounded by cell clumping. The HEK293 DKO 10 L wavebag transfection showed more significant clumping (data not shown), higher final day lactate levels (FIG. 6B), and lower oxygen levels (FIG. 6D) compared to the 30 mL tubespin cultures. Despite differences in cell clumping, lactate, and oxygen, cells from both vessel types consumed glucose at a similar rate (FIG. 6B), exhibited similar osmolality and pH profiles (FIG. 6C), and produced comparable final titers (FIG. 6E). These data demonstrate HEK293 DKO transfection methodologies that produced similar titers in large scale 10 L wavebags and 30 mL tubespins. Using the described wavebag system for production, instead of a stirred-tank bioreactor, eliminates the need for probes and online measurements as well as cleaning and sterilization steps between production runs. This provides significant resource savings and operational benefits for executing high throughput large scale transfections to generate material for biopharmaceutical research efforts to identify therapeutic candidates.

Combined, the optimized HEK293 DKO 35 L bioreactor seed train and 10 L transient transfection processes described herein enable the high throughput generation of recombinant proteins to support research studies leading to the identification of therapeutic clinical candidates.

Transient transfection of HEK293 cells has been established as a method to quickly produce recombinant proteins for antibody and large molecule discovery campaigns to identify therapeutic candidates. An anti-apoptotic HEK293 cell line was engineered by deleting pro-apoptotic genes Bax and Bak. The HEK293 Bax Bak double knock out (HEK293 DKO) cell line was resistant to apoptosis and shear stress, and the cells were used to optimize and implement a 35 L bioreactor seed train and a 10 L high titer transient production process. A regularly passaged bioreactor seed train (i.e. split every 3-4 days) was most productive when a pH setpoint of 7.0, a narrow pH deadband of ±0.03, and a DO setpoint of 30% were used. A 35 L bioreactor seed train provided enough cells to start up to 70 L of transfections twice per week for up to 60 days. This is thought to be the first report of long term cultivation of HEK293 seed train in a pilot scale bioreactor to source cells for routine transfections. To optimize transient production process, ambr15 microbioreactors were used to test pH and agitation parameters, and it was found that highest titers occurred when a pH setpoint of 7.0, a wide pH deadband of ±0.4, and an agitation of 630 rpm were used. Targeting similar pH to a wide pH deadband, the transient production process was scaled up to 10 L wavebags without direct pH control. HEK293 DKO transient transfections at all scales tested produced high antibody titers, up to 650 mg/L in 7 days. Development of a HEK293 DKO 35 L bioreactor seed train and a 10 L high titer production process enables efficient, high throughput generation of recombinant proteins for research and pre-clinical studies.

What is claimed is:

1. A method of producing a recombinant polypeptide, comprising:

culturing a HEK293 cell line that comprises (a) a loss-of-function mutation in each of the human Bax and Bak genes and (b) a polynucleotide encoding the recombinant polypeptide, under conditions suitable for production of the polypeptide, wherein the loss of function mutation is a deletion in each of the Bax and Bak genes and wherein a polyethylenimine (PEI): DNA ratio of 7.5 and a DNA concentration of 1 μg/mL was used for transfection of the polynucleotide, wherein the cell line is cultured:

(a) at a pH of between about 6.7 and about 7.3;

(b) with a dissolved oxygen (DO) setpoint of about 30%; and (c) at an agitation rate that imparts a power input per volume (P/V) of about 13 W/m$^3$.

2. The method of claim 1, wherein the polynucleotide that encodes the recombinant polypeptide is an extrachromosomal polynucleotide.

3. The method of claim 1, wherein the recombinant polypeptide is an antibody or antigen-binding fragment thereof.

4. The method of claim 3, wherein the cell line produces the recombinant polypeptide at a titer of about 650 mg/L in 7 days.

5. The method of claim 4, wherein the cell line maintains at least 85% cell viability after being cultured for 60 days in a 35 L bioreactor culture.

6. The method of claim 4, wherein the cell line is cultured in the 35 L bioreactor culture at a working volume of between about 20 L and about 35 L.

7. The method of claim 4, wherein the cell line is cultured under fed-batch culture conditions.

8. The method of claim 4, wherein the cell line is cultured under perfusion culture conditions.

* * * * *